US007049304B2

(12) United States Patent
Holmes-Farley et al.

(10) Patent No.: US 7,049,304 B2
(45) Date of Patent: May 23, 2006

(54) ARYL BORONIC ACIDS FOR TREATING OBESITY

(75) Inventors: Stephen Randall Holmes-Farley, Arlington, MA (US); W. Harry Mandeville, III, Lynnfield, MA (US); Pradeep K. Dhal, Westford, MA (US); Chad Cori Huval, Somerville, MA (US); Xinhua Li, Newton, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 11/027,643

(22) Filed: Dec. 30, 2004

(65) Prior Publication Data

US 2005/0107336 A1    May 19, 2005

Related U.S. Application Data

(63) Continuation of application No. 10/187,397, filed on Jun. 27, 2002, now Pat. No. 6,858,592.

(60) Provisional application No. 60/359,467, filed on Feb. 22, 2002, provisional application No. 60/302,081, filed on Jun. 29, 2001.

(51) Int. Cl.
 *A61K 31/69* (2006.01)
 *C07F 5/02* (2006.01)

(52) U.S. Cl. .................. 514/64; 558/44; 562/7
(58) Field of Classification Search ............... 514/64; 558/44; 562/7
 See application file for complete search history.

(56) References Cited

U.S. PATENT DOCUMENTS

| 4,496,722 A | 1/1985 | Gallop et al. |
|---|---|---|
| 5,290,817 A | 3/1994 | Petraitis |
| 5,356,893 A | 10/1994 | Bradshaw et al. |
| 5,472,628 A | 12/1995 | Panandiker et al. |
| 5,631,371 A | 5/1997 | Bloczynski |
| 5,702,952 A | 12/1997 | Sundrehagen et al. |
| 5,726,343 A | 3/1998 | Ziegler et al. |
| 5,739,318 A | 4/1998 | Frantzen et al. |

(Continued)

FOREIGN PATENT DOCUMENTS

| DE | 3930663 | 11/1990 |
|---|---|---|
| DE | 4307243 | 10/1993 |
| EP | 0 354 434 | 2/1990 |
| EP | 0 478 050 | 4/1992 |
| EP | 0 495 627 | 7/1992 |
| EP | 0 571 928 | 12/1993 |
| EP | 1 072 597 | 1/2001 |
| GB | 2 276 162 | 9/1994 |

(Continued)

OTHER PUBLICATIONS

Medline, abstract No. 11234459, Obesity:preventing and managing the global epidemic. Report of a WHO consultation, World Health Orgainzation technical report series, (2000) 894 i-xii, 1-253.*

Barba, V., et al., "Synthesis and molecular structures of dimeric boron compounds", J. Organometallic Chem., 604:273-282 (2000).

(Continued)

*Primary Examiner*—Porfirio Nazario-Gonzalez
(74) *Attorney, Agent, or Firm*—Fish & Neave IP Group Ropes & Gray, LLP

(57) ABSTRACT

Disclosed is a phenyl boronic acid compound represented by Structural Formula (I):

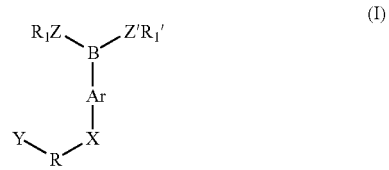

Ar is a substituted or unsubstituted aryl group.
 Z and Z' are independently —O—, —NH— or —S—.
 X is an electron withdrawing group.
 R is a substituted or unsubstituted straight chained hydrocarbyl group optionally comprising one or more amine, ammonium, ether, thioether or phenylene linking groups and Y is —H, an amine, —[NH—$(CH_2)_q$]$_r$—$NH_2$, halogen, —$CF_3$, thiol, ammonium, alcohol, —COOH, —$SO_3H$, —$OSO_3H$ or phosphonium group covalently bonded to the terminal position of R. Each —NH— in —[NH—$(CH_2)_q$]$_r$—$NH_2$ is optionally N-alkylated or N,N-dialkylated and —$NH_2$ in —[NH—$(CH_2)_q$]$_r$—$NH_2$ is optionally N-alkylated, N,N-dialkylated or N,N,N-trialkylated.
 q is an integer from 2 to about 10 and r is an integer from 1 to about 5.
 $R_1$ and $R_{1'}$ are independently —H, an aliphatic group, a substituted aliphatic group, an aryl group or a substituted aryl group, or, taken together, are a C2–C5 substituted or unsubstituted alkylene group optionally comprising an amine linking group [—$N^+(R^{1a})$—].
 Each $R_1$ is Structural Formula (I) is preferably —H.
 $R^{1a}$ is —H, alkyl, substituted alkyl, phenyl or substituted phenyl.

Also disclosed is a method of treating obesity in a subject by administering an effective amount of a compound represented by Structural Formula (I) and a pharmaceutical composition comprising the compound and a pharmaceutically acceptable carrier or diluent.

39 Claims, 9 Drawing Sheets

U.S. PATENT DOCUMENTS

| | | | |
|---|---|---|---|
| 5,840,677 | A | 11/1998 | Nielsen et al. |
| 5,866,568 | A | 2/1999 | Bradbury et al. |
| 5,972,873 | A | 10/1999 | Nielsen et al. |
| 6,184,363 | B1 | 2/2001 | Shoichet et al. |
| 6,197,967 | B1 | 3/2001 | Vollmueller et al. |
| 6,264,937 | B1 | 7/2001 | Mandeville, III et al. |
| 6,858,592 | B1 | 2/2005 | Holmes-Farley et al. |
| 2004/0038940 | A1 | 2/2004 | Caron et al. |

FOREIGN PATENT DOCUMENTS

| | | |
|---|---|---|
| JP | 2000336045 | 12/2000 |
| JP | 3257029 B2 | 12/2001 |
| JP | 2002265472 | 9/2002 |
| WO | WO-92/08722 | 5/1992 |
| WO | WO-94/14803 | 7/1994 |
| WO | WO-95/01326 | 1/1995 |
| WO | WO-95/11243 | 4/1995 |
| WO | WO-95/20569 | 8/1995 |
| WO | WO-96/02288 | 2/1996 |
| WO | WO-96/17833 | 6/1996 |
| WO | WO-96/21716 | 7/1996 |
| WO | WO-96/30333 | 10/1996 |
| WO | WO-96/40681 | 12/1996 |
| WO | WO-97/30055 | 8/1997 |
| WO | WO-98/22820 | 5/1998 |
| WO | WO-98/47885 | 10/1998 |
| WO | WO-98/56392 | 12/1998 |
| WO | WO-99/05107 | 2/1999 |
| WO | WO-99/23073 | 5/1999 |
| WO | WO-99/47474 | 9/1999 |
| WO | WO-00/06537 | 2/2000 |
| WO | WO-00/14083 | 3/2000 |
| WO | WO-00/27394 | 5/2000 |
| WO | WO-00/27820 | 5/2000 |
| WO | WO-00/35904 | 6/2000 |
| WO | WO-00/42213 | 7/2000 |
| WO | WO-00/61571 | 10/2000 |
| WO | WO-01/16108 | 3/2001 |
| WO | WO-2002044189 | 6/2002 |
| WO | WO-2003106384 | 12/2003 |

OTHER PUBLICATIONS

CA:119:139268 abs of EP 533266 Mar. 1993.
CA:120:218155 abs JP 05301880 Nov. 1993.
CA:126:144291 abs of WO 960681 Dec. 1996.
CA:132:331255 abs of Biorganic & Medicinal Chem by DeSantis et al. 8(3) pp. 563-570 2000.
CA:137:249492 abs of JP2002265472 Sep. 2002.
CA:137:26190 abs of WO 2002044189 Jun. 2002.
CA:140:59511 abs of WO 2003106384 Dec. 2003.
CA:79:106049 abs of Journal of Applied Polymer Science by Leipins et al. 17 (8) pp. 2523-2532 (1973).
Deantis, G., et al., "Benzophenone boronic acid photoaffinity labeling of subtilisin CMMs to probe altered specificity," Bioorganic and Medicinal Chemistry, 8(3):563-570 (2000).
Draffin, S.P., et al., "Highly Fructose Selective Transport Promoted by Boronic Acids Based on a Pentaerythritol Core," American Chemical Society, Organic Letters, 3(6):917-920 (2001).
English patent abstract of JP 2002-265472.
English patent abstract of JP 3257029B2.
Folch, J., et al., "A Simple Method For The Isolation and Purification of Total Lipides From Animal Tissues", J. Biol. Chem., 226:497 (1957).
Gravel, M., et al., "Universal Solid-Phase Approach for the Immobilization, Derivatization, and Resin-to-Resin Transfer reactions of Boronic Acids," J. Org. Chem., 67:3-15 (2002).
Hall, D.G., et al., "N, N-Diethanolaminomethyl Polystyrene: An Efficient Solid Support to Immobilze Boronic Acids," Angew. Chem. Int. Ed., 38(20):3064-3067 (1998).
Hall, D.G., et al., "N,N-Diethanolaminomethylpolystyrol: ein effizienter fester Träger für die Immobilisierung van Boronsäuren," Angew. Chem. Int., 111:3250-3253 (1999).
Hall, I., et al., "Hypolipidemic, Anti-obesity, Anti-inflammatory, Anti-osteoporotic, and Anti-neoplastic Properties of Amine Carboxyboranes," Environ. Health Perspect. Suppl. 102(S3):21-30 (1994).
Hansch, C., et al., "Hammett Sigmas," Exploring QSAR Hydrophobic, Electronic and Steric Constants, American Chemical Society, 217-232 (1995).
Ishiyama, T., et al., "Palladium(0)-Catalyzed Cross-Coupling Reaction of Alkoxydiboron with Haloarenes: A Direct Procedure for Arylboronic Esters", J. Org. Chem., 60(23):7508-7510 (1995).
Kinder, D. H., et al., "Synthesis of 2-Amino-3-Boronopropionic Acid: A Boron-Containing Analogue of Aspartic Acid," J. Org. Chem., 52(12):2452-2454 (1987).
Kobayashi, Y., et al., "Preparation of Functionalized Zinc Borates an their Coupling Reaction with Allylic Acetates," Tetrahedron Lett., 39:7537-7540 (1998).
Leipins, R. et al., "Organoboron compounds as durable flame retardants for cotton fabric," Journal of Applied Polymer Science, 17(8):2523-32 (1973).
Matteson, D. S., et al., "Directed Chiral Synthesis with Pinanediol Boronic Esters", J. Am. Chem. Soc., 102(25):7590-7591 (1980).
Reuman, M., et al., "Synthesis and Antibacterial Activity of Some Novel 1-Substituted 1, 4-Dihydro-4-Oxo-7-pyridinyl-3-quinolinecarboxylic acids. Potent Antistaphylococcal Agents." J. Med. Chem., 38(14):2531-2540 (1995).
Saito, S., et al., "Synthesis of Biaryls via a Nickel(0)-Catalyzed Cross-Coupling Reaction of Chloroarenes with Arylboronic Acids", J. Org. Chem. 62:8024-8030 (1997).
Sakai, M., et al., "Rhodium-Catalyzed Addition of Organoboronic Acids to Aldehydes", Angew. Chem. Int. Ed. 37(23):3279-3281 (1998).

* cited by examiner

ARYL BORONIC ACIDS FOR TREATING OBESITY

RELATED APPLICATION(S)

This application is a continuation of U.S. application Ser. No. 10/187,397, filed Jun. 27, 2002, now U.S. Pat. No. 6,858,592, which claims the benefit of U.S. Provisional Application No. 60/302,081, filed Jun. 29, 2001 and U.S. Provisional Application No. 60/359,467, filed Feb. 22, 2002. The entire teachings of the above application(s) are incorporated herein by reference.

BACKGROUND OF THE INVENTION

Human obesity is a recognized health problem with approximately ninety-seven million people considered clinically overweight in the United States. Various chemical approaches have been used for treating obesity. In one such approach, a medicament which inhibits lipases is administered to the obese patient. Lipases are key enzymes in the digestive system which break down diglycerides and triglycerides into monoglycerides and fatty acids. Diglycerides and triglycerides have a high caloric content but are not absorbed by the small intestine until broken down by the lipases. Therefore, inhibition of lipases within the digestive system results in a reduction in the absorption of fat and consequently a decrease in caloric uptake. XENICAL is an example of a commercially available lipase inhibitor that is used for treating obesity.

There is still a need, however, for improved lipase inhibitors. For example, administration of lipase inhibitors results in stools with a high fat or oil content from the undigested diglycerides and triglycerides. Leakage of oil from the stool is an unpleasant side effect that often occurs when stools have a high fat or oil content. This condition is referred to as "oily stool" or "leaky stool". It has been reported in U.S. application Ser. No. 09/166,453 that fat-binding polymers, when co-administered with lipase inhibitors, can bind with or "stabilize" the oil and thereby reduce or eliminate the leakage of oil from the stool. It would be desirable to develop a single compound which is both a lipase inhibitor and a fat-binder. In addition, a lipase inhibitor should be minimally absorbed by the intestines to prevent systemic side-effects. Other desirable features include ease and economy of manufacture.

SUMMARY OF THE INVENTION

The present invention is directed to novel aryl boronic acids and derivatives thereof which are effective lipase inhibitors (Examples 11 and 12). Many of these compounds are readily attached to fat-binding polymers comprising alcohol or diol functionalities by means of boronate ester, boronate thioester and/or boronamide bonds. These bonds are believed to be hydrolyzed in vivo, thereby resulting in the delivery of a lipase inhibitor and a fat-binding polymer to the gastrointestinal tract. Based on these discoveries, novel aryl boronic acids and derivatives thereof, pharmaceutical compositions comprising these aryl boronic acids and derivatives and methods of treating obesity with a novel aryl boronic acid or a derivative thereof are disclosed herein.

One embodiment of the present invention is a compound represented by Structural Formula (I):

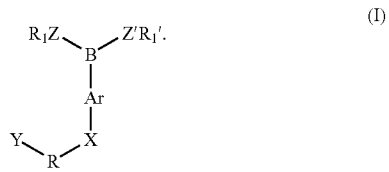

Z and Z' are independently —O—, —NH— or —S—. Preferably, Z and Z' are both —O—.

Ar is a substituted (e.g., monosubstituted or polysubstituted) or unsubstituted aryl group.

X is an electron withdrawing group.

R is a substituted or unsubstituted straight chained hydrocarbyl group optionally comprising one or more amine, ammonium, ether, thioether or phenylene linking groups and Y is —H, an amine, —[NH—$(CH_2)_q$]$_r$—$NH_2$, halogen, —$CF_3$, thiol, ammonium, alcohol, —COOH, —$SO_3H$, —$OSO_3H$ or phosphonium group covalently bonded to the terminal position of R. Preferably, when Y is —H and R is a straight chained hydrocarbyl group, then R has from 1 to 30 carbon atoms, preferably 4 to 30 carbon atoms, (more preferably from 6 to 30 carbon atoms, even more preferably from 8 to 30 carbon atoms and even more preferably from 10 to 30 carbon atoms). Each —NH— in —[NH—$(CH_2)_q$]$_r$—$NH_2$ is optionally N-alkylated or N,N-dialkylated and —$NH_2$ in —[NH—$(CH_2)_q$]$_r$—$NH_2$ is optionally N-alkylated, N,N-dialkylated or N,N,N-trialkylated.

$R_1$ and $R_1$' are independently —H, an aliphatic group, a substituted aliphatic group, an aryl group or a substituted aryl group, or, taken together, a C2–C5 substituted or unsubstituted alkylene group optionally comprising an amine linking group [—$N^+(R^{1a})$—]. Preferably, $R_1$ and $R_1$' in Structural Formula (I) are both —H.

$R^{1a}$ is —H, alkyl, substituted alkyl, phenyl or substituted phenyl.

q is an integer from 2 to about 10 and r is an integer from 1 to about five.

Another embodiment of the present invention is a pharmaceutical composition. The pharmaceutical composition comprises the compound described above and a pharmaceutically acceptable carrier or diluent. Preferably, the pharmaceutical composition comprises an effective concentration of the compound.

Another embodiment of the present invention is a method for removing fat from the gastrointestinal tract (or inhibiting uptake of fat in the gastrointestinal tract) of a subject in need of such treatment (e.g., treating a subject for obesity). The method comprises the step of administering an effective amount of the compound described above to the subject.

The aryl boronic acids and aryl boronic acid derivatives of the present invention are potent lipase inhibitors. Thus, they are effective for the treatment of obesity. Moreover, many of these compounds can be attached to fat-binding polymers. These boron functionalized polymers can also be used to treat obesity, but have the advantage of not causing the "oily stools" normally associated with lipase inhibitors. The aryl boronic acids and aryl boronic acid derivatives disclosed herein are thus precursors to these improved polymer drugs.

DETAILED DESCRIPTION OF THE INVENTION

Figure 1:
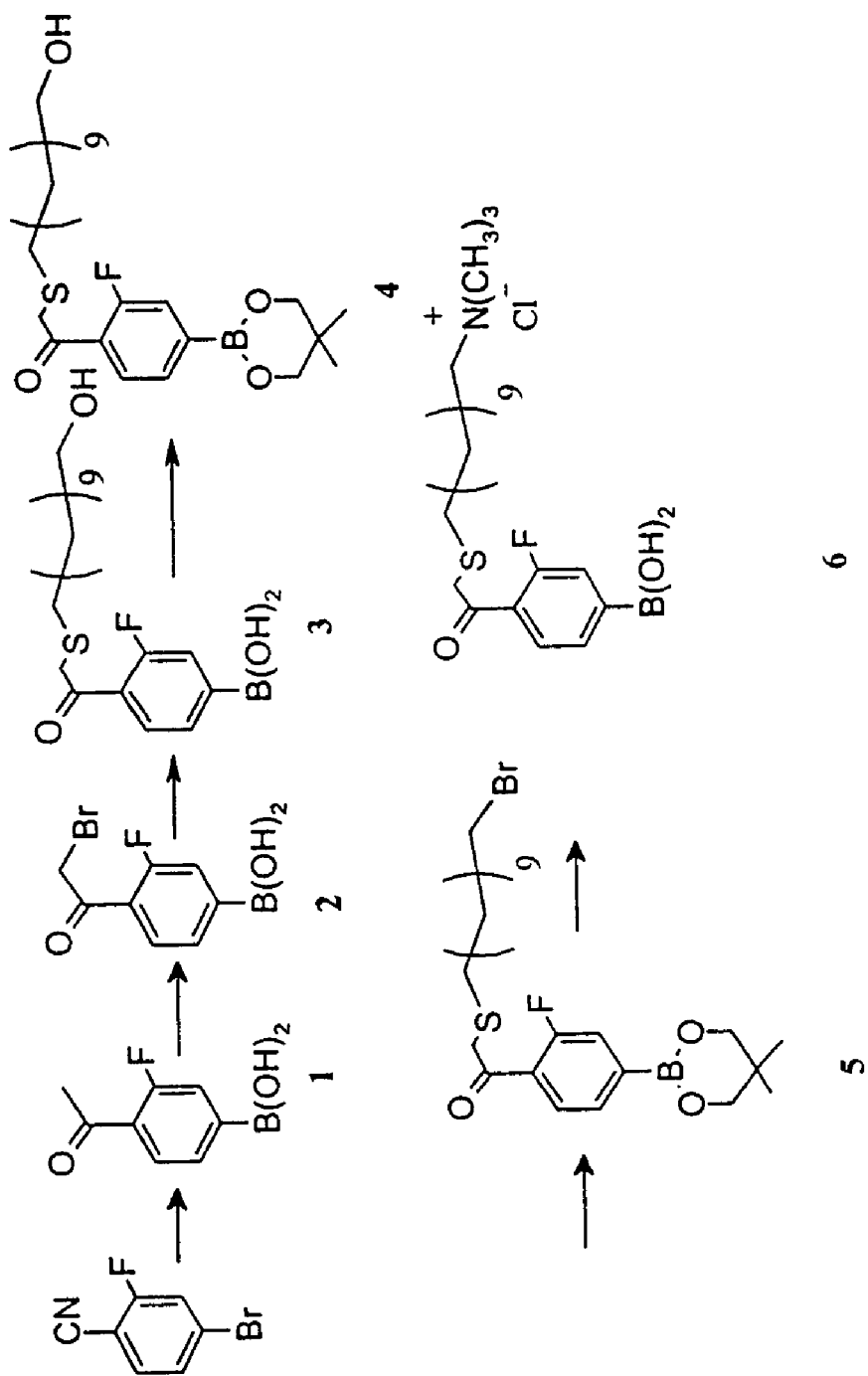
FIG. 1 is a schematic showing the synthesis of 4-(14'-trimethylammonium-3'-thia-1'-ketotetradecyl)-3-fluorophenylboronic acid chloride (6).

The invention is described below with respect to aryl boronic acids and aryl boronate esters, i.e., wherein Z and Z' are both —O—. It is to be understood that these descriptions apply to the corresponding boronamides and boronate thioesters, i.e., wherein one or both of Z and Z' are —NH— or —S—.

Ar in Structural Formula (I) is substituted or unsubstituted. Ar is "substituted" when it comprises at least one substituent in addition to the boronic acid group and the —X—R—Y group. Suitable substituents are as described below for aryl groups.

—X— is an electron withdrawing group. As used herein, an "electron withdrawing group" is a substituent which results in a phenyl ring that has less electron density when the group is present than when it is absent. Electron withdrawing groups have a Hammet sigma value greater than one (see, for example, C. Hansch, A. Leo and D. Hoeckman, "Exploring QSAR Hydrophobic, Electronic and Steric Constants", American Chemical Society (1995), pages 217–32) Examples of suitable values for X include —CHZ-, —CZ$_2$-, —COO—, —CON($R^{1b}$)—, —CO— or —SO$_2$—. Other suitable values of X include —S(O)— and —S(O)$_2$O—. Z is a halogen and $R^{1b}$ is —H, alkyl or substituted alkyl (preferably —R—Y). In the compounds of the present invention, Phenyl Ring A is preferably substituted with one or more electron withdrawing groups in addition to —X—. Suitable examples include halogens, —NO$_2$ and —CN; fluorine is a preferred example.

A "straight chained hydrocarbyl group" is an alkylene group, i.e., —(CH$_2$)$_x$— where x is a positive integer (e.g., from 1 to about 30), preferably between 6 and about 30, more preferably between about 6 and about 15. A "linking group" refers to a functional group which replaces a methylene in a straight chained hydrocarbyl. Examples of suitable linking groups include an alkene, alkyne, phenylene, ether (—O—), thioether (—S—), amine [—N$^+$($R^a$)—] or ammonium [—N$^+$($R^a R^b$)—]. $R^a$ and $R^b$ are independently —H, alkyl, substituted alkyl, phenyl, substituted phenyl, or, taken together with the nitrogen atom to which they are bonded, a non-aromatic, nitrogen-containing heterocyclic group. Preferably, $R^a$ and $R^b$ are not —H. More preferably, $R^a$ and $R^b$ are both alkyl groups and even more preferably, both methyl. $R^a$ and $R^b$ can be the same or different, but are preferably the same.

The terms "terminal position" or "terminus" refer to the methylene carbon of the straight chained hydrocarbyl group most distant from Ar. Substituents at the terminal position of a straight chained hydrocarbyl group are referred to herein as "terminal substituents". As noted above, a number of compounds of the present invention have an amine (—NR$^c$R$^d$) or ammonium (—N$^+$R$^c$R$^d$R$^e$) group as a terminal substituent of the hydrocarbyl group represented by R. R$^c$, R$^d$ and R$^e$ in an ammonium group are independently —H, alkyl, substituted alkyl, phenyl, substituted phenyl, or, taken together with the nitrogen atom to which they are bonded, a nitrogen-containing, non-aromatic heterocyclic group. Preferably, R$^c$, R$^d$ and R$^e$ are not —H. More preferably, R$^c$, R$^d$ and R$^e$ are all alkyl groups (i.e., a trialkylammonium group) and even more preferably, all methyl (i.e., a trimethylammonium group). R$^c$, R$^d$ and R$^e$ can be the same or different, but are preferably all the same.

In one example Y is selected such that YH is a small molecule polyamine (H—[NH—(CH$_2$)$_q$]$_r$—NH$_2$) such as spermine, spermidine, 1,2-diaminoethane, 1,3-diaminopropane or 1,4-diaminobutane. Optionally, one or more of the secondary amine can optionally be N-alkylated or N,N-dialkylated; the primary amine is optionally N-alkylated, N,N-dialkylated or N,N,N-trialkylated.

A "substituted hydrocarbyl group" has one or more substituents bonded at one or more positions other than at the terminus. Suitable substituents are those which do not significantly lower the lipase inhibiting ability or fat binding ability of the polymer, for example, do not lower either activity by more than a factor of about two. Examples of suitable substituents include C1–C3 straight chained or branched alkyl, C1–C3 straight chained or branched haloalkyl, —OH, halogen (—Br, —Cl, —I and —F), —O(C1–C3 straight chain or branched alkyl) or —O(C1–C3 straight chain or branched haloalkyl).

In a preferred embodiment, the compound of the present invention is represented by Structural Formula (II):

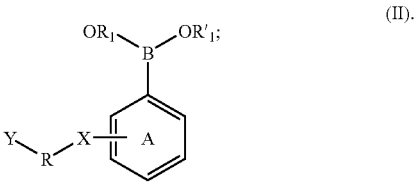

(II).

Phenyl Ring A is substituted or unsubstituted. Phenyl Ring A is "substituted" when it comprises at least one substituent in addition to the boronic acid group and the —X—R—Y group. Suitable substituents are as described below for aryl groups.

R, R$_1$, R'$_1$, X and Y in Structural Formula (II) are as described for Structural Formula (I). Preferably, Y—R—X— is para to —B(OR$_1$)(OR'$_1$).

In a more preferred embodiment, the compound of the present invention is represented by Structural Formula (III):

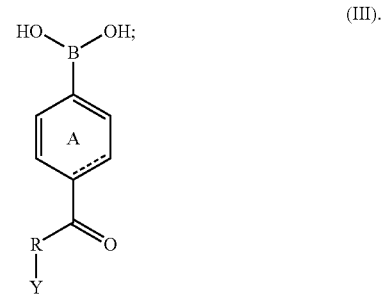

(III).

Phenyl Ring A, R and Y in Structural Formula (III) are as described above for Structural Formula (II). Phenyl Ring A is preferably substituted with zero, one or more independently selected electron withdrawing groups represented by R$_2$.

R in Structural Formulas (II) and (III) is a substituted or unsubstituted straight chained hydrocarbyl group optionally comprising one or more ether, thioether, phenylene, amine, or ammonium linking groups. Preferred linking groups for R in Structural Formulas (II) and (III) are ether or thioether. Alternatively, R in Structural Formulas (II) and (III) is —CH$_2$—O[—(CH$_2$)$_p$O]$_m$—(CH$_2$)$_p$— or —CH$_2$—S[—(CH$_2$)$_p$O]$_m$—(CH$_2$)$_p$—; p is 2 or 3; and m is an integer from 1–8.

Y in Structural Formulas (II) and (III) is preferably an amine or ammonium group covalently bond to the terminal position of R, more preferably a trialkylammonium group bonded to the terminal position of R and even more preferably a trimethylammonium group bonded to the terminal position of R.

In a more preferred embodiment, the compound of the present invention is represented by Structural Formulas (IV) and (V):

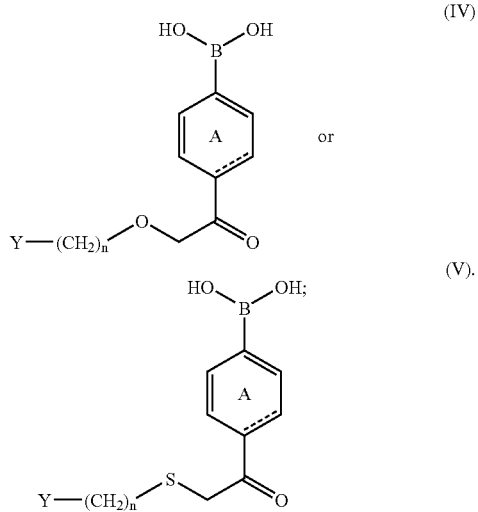

Phenyl Ring A in Structural Formulas (IV) and (V) is as described for Structural Formulas (II)–(III).

Y in Structural Formulas (IV) and (V) is a trialkylammonium group.

n is an integer from about 6 to about 30, preferably from about 6 to about 15.

Preferably in Structural Formulas (IV) and (V), Y is trimethylammonium, Phenyl Ring A is substituted with one or two fluorine groups and n is as defined above. Examples of suitable substitution patterns for Phenyl Ring A include 3-fluoro and 2,5-difluoro, wherein the carbon bonded to boron is considered to be carbon one.

Also included in the present invention are boronate esters of the boronic acids represented by Structural Formulas (III)–(V). A boronate ester is obtained by replacing one or both boronic acid hydrogen atoms with R$_1$, as described in Structural Formulas (I) and (II). It is believed that boronate esters are hydrolyzed in the gastrointestinal tract to form boronic acids, which then act as lipase inhibitors.

Also included in the present invention are the boronamides or boronate thioesters corresponding to the boronate esters described in the previous paragraph. The boronamide or boronate thioester is obtained by independently replacing one or both boronate ester oxygen atoms with —S— or —NH—.

As used herein, aliphatic groups include straight chained, branched or cyclic C1–C30 (preferably C1–C15) hydrocarbons which are completely saturated or which contain one or more units of unsaturation. Preferred aliphatic groups are completely saturated and acyclic, i.e., straight chained or branched alkyl groups or alkylene groups. Suitable substituents for an aliphatic group are those which do not significantly lower the lipase inhibiting ability of the compound, for example, do not lower either activity by more than a factor of about two. Examples include —OH, halogen (—Br, —Cl, —I and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH and —S(R'). Each R' is independently an alkyl group or an aryl group. A substituted aliphatic group can have more than one substituent.

Aryl groups include carbocyclic aromatic groups such as phenyl and naphthyl, heteroaryl groups such as imidazolyl, thienyl, furanyl, pyridyl, pyrimidy, pyranyl, pyrazolyl, pyrazinyl, thiazole, oxazolyl and fused polycyclic aromatic ring systems in which a carbocyclic aromatic ring or heteroaryl ring is fused to one or more other heteroaryl rings (e.g., benzothienyl, benzofuranyl, indolyl, quinolinyl, benzothiazole, benzooxazole, benzimidazole and quinolinyl). Suitable substituents for an aryl group are those which do not significantly lower the lipase inhibiting ability of the compound, for example, do not lower either activity by more than a factor of about two. Examples include alkyl, halogenated alkyl, —OH, halogen (—Br, —Cl, —I and —F), —O(R'), —O—CO—(R'), —CN, —NO$_2$, —COOH, —NH$_2$, —NH(R'), —N(R')$_2$, —COO(R'), —CONH$_2$, —CONH(R'), —CON(R')$_2$, —SH and —S(R'). Each R' is independently an alkyl group or an aryl group. A substituted aryl group can have more than one substituent.

Non-aromatic nitrogen-containing, heterocyclic rings are non-aromatic carbocyclic rings which include at least one nitrogen atom and, optionally, one or more other heteroatoms such as oxygen or sulfur in the ring. The ring can be five, six, seven or eight-membered. Examples include morpholino, thiomorpholino, pyrrolidinyl, piperazinyl and piperidinyl.

Also included in the present invention are pharmaceutically acceptable salts of the disclosed compounds. For example, compounds which have acid functional groups can be present in the anionic, or conjugate base, form, in combination with a cation. Suitable cations include alkaline earth metal ions, such as sodium and potassium ions, alkaline earth ions, such as calcium and magnesium ions, and unsubstituted and substituted (primary, secondary, tertiary and quaternary) ammonium ions. Compounds which have basic groups such as amines can be present in a protonated form together with a pharmaceutically acceptable counter anion, such as chloride, bromide, acetate, formate, citrate, ascorbate, sulfate or phosphate. Similarly, ammonium groups comprise a pharmaceutically acceptable counteranion. Boronic acid groups can react with anions such as sodium or potassium hydroxide, alkoxide or carboxylate to form a salt such as —B$^-$(OH)$_3$Na$^+$, —B$^-$(OH)$_3$K$^+$, —B$^-$(OH)$_2$(OCH$_3$)Na$^+$, —B$^-$(OH)$_2$(OCH$_3$)K$^+$, —B$^-$(OH)$_2$(OCOCH$_3$)Na$^+$, —B$^-$(OH)$_2$(OCOCH$_3$)K$^+$, and the like.

A "subject" is preferably a mammal, such as a human, but can also be a companion animal (e.g., dogs, cats, and the like), farm animals (e.g., cows, sheep, pigs, horses, and the like) or laboratory animals (e.g., rats, mice, guinea pigs, and the like) in need of treatment for obesity.

The compounds of the present invention are suitable as a medicament for promoting weight reduction in subjects because they inhibit lipases in the gastrointestinal tract. As such, they are administered in a manner suitable for reaching the gastrointestinal tract during digestion. They are therefore preferably administered orally as soon as up to about one hour prior to a meal and as late as up to about one hour subsequent to a meal. Alternatives modes of administration are also possible, including rectal, nasal, pulmonary and topical administration.

The compounds of the present invention are administered to inhibit of uptake of fat in the gastrointestinal tract (or to promote removal of fat from the gastrointestinal tract). Thus, they can be also be advantageously used to in the treatment or one or more of the following conditions: obesity, Type II (non-insulin-dependent) diabetes mellitus, impaired glucose tolerance, hypertension, coronary thrombosis, stroke, lipid syndromes, hyperglycemia, hypertriglyceridemia, hyperlipidemia, sleep apnea, hiatal hernia, reflux esophagisitis, osteoarthritis, gout, cancers associated with weight gain, gallstones, kidney stones, pulmonary hypertension, infertility, cardiovascular disease, above normal weight, and above normal lipid levels; or where the subject would benefit from reduced platelet adhesiveness, weight loss after pregnancy, lowered lipid levels, lowered uric acid levels, or lowered oxalate levels. A subject with one or more of these conditions is said to be "in need of treatment" with an agent that inhibits absorption of fat from the gastrointestinal tract.

The compounds can be administered to the subjects in conjunction with an acceptable pharmaceutical carrier as part of a pharmaceutical composition for treatment of obesity. Formulations vary according to the route of administration selected, but are typically capsules, tablets or powder for oral administration. Solutions and emulsions are also possible. Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Methods for encapsulating compositions (such as in a coating of hard gelatin or cyclodextran) are known in the art (Baker, et al., "Controlled Release of Biological Active Agents", John Wiley and Sons, 1986).

An "effective amount" is the quantity of compound which results in a greater amount of weight reduction over a period of time during which a subject is being treated with the aryl boronic acid drug for obesity compared with the corresponding time period in absence of such treatment. Typical dosages range from about 5 mg/day to about 10 grams/day, preferably from about 5 mg/day to about 5 grams/day. The compound can be administered alone or in a pharmaceutical composition comprising the compound, an acceptable carrier or diluent and, optionally, one or more additional drugs, typically one or more additional drugs used for weight reduction (e.g., XENICAL or MERIDIA). The precise amount of drug being administered to a subject will be determined on an individual basis and will depend on, at least in part, the subject's individual characteristics, such as general health, age, sex, body weight and tolerance to drugs, and the degree to which the subject is overweight and the amount of weight reduction sought.

An "effective concentration" is the concentration of compound present in a pharmaceutical composition which, when divided into a unit dosage form, provides an effective amount of the compound.

The aryl boronic acid compounds of the present invention can also be reacted to form boronate esters with pharmaceutically acceptable polymers having free alcohol or diol groups and administered as a polymer drug. Reactions for forming boronate ester bonds are well known in the art and include refluxing the boronic acid and diol in an appropriate solvent (e.g., alcohol, toluene, methylene chloride, tetrahydrofuran (THF) or dimethyl sulfoxide (DMSO)). Alternatively, an aryl boronic acid can be to a polymer having free alcohol or diol groups by means of a transesterification reaction, as described in D. H. Kinder and M. M. Ames, *Journal of Organic Chemistry* 52:2452 (1987) and D. S. Matteson and R. Ray, *Journal of American Chemical Society* 102:7590 (1980), the entire teachings of which are incorporated herein by reference.

The boronate ester of these polymer drugs is believed to be hydrolyzed in the gastrointestinal tract to release the aryl boronic acid, which can then act to inhibit lipase enzymes. Preferably, the polymer is a fat-binding polymer. After hydrolysis of the aryl boronate ester to release the aryl boronic acid, the fat-binding polymer is then available to absorb the diglyercides and triglycerides which remain undigested as a result of inhibition of the lipase enzymes by the released aryl boronic acid. The undesired side-effect of "oily stools" is thereby minimized or eliminated through the use of these polymer drugs. "Fat-binding polymers" are polymers which absorb, bind or otherwise associate with fat thereby inhibiting (partially or completely) fat digestion, hydrolysis, or absorption in the gastrointestinal tract and/or facilitate the removal of fat from the body prior to digestion. The fat-binding polymers generally comprise one or more fat-binding regions. "Fat-binding regions" include a positively charged region and, optionally, a hydrophobic region, or a region which is both positively charged and hydrophobic. The fat-binding region has a positive charge when the region comprises an ionic group such as a quarternary amine or an atom, for example, the nitrogen of an amine, that possesses a positive charge under conditions present in the gastrointestinal tract. The attachment of artl boronic acid lipase inhibitors to fat-binding polymers and the use of these polymers as anti-obesity drugs are described in the co-pending U.S. Provisional Application Ser. No. 60/302,221, entitled "Aryl Boronate Functionalized Polymers for Treating Obesity," filed on Jun. 29, 2001, and U.S. Provisional Application Ser. No. 60/359,473, entitled "Aryl Boronate Functionalized Polymers for Treating Obesity," filed Feb. 22, 2002. The entire teachings of this application are incorporated herein by reference.

Figure 2:
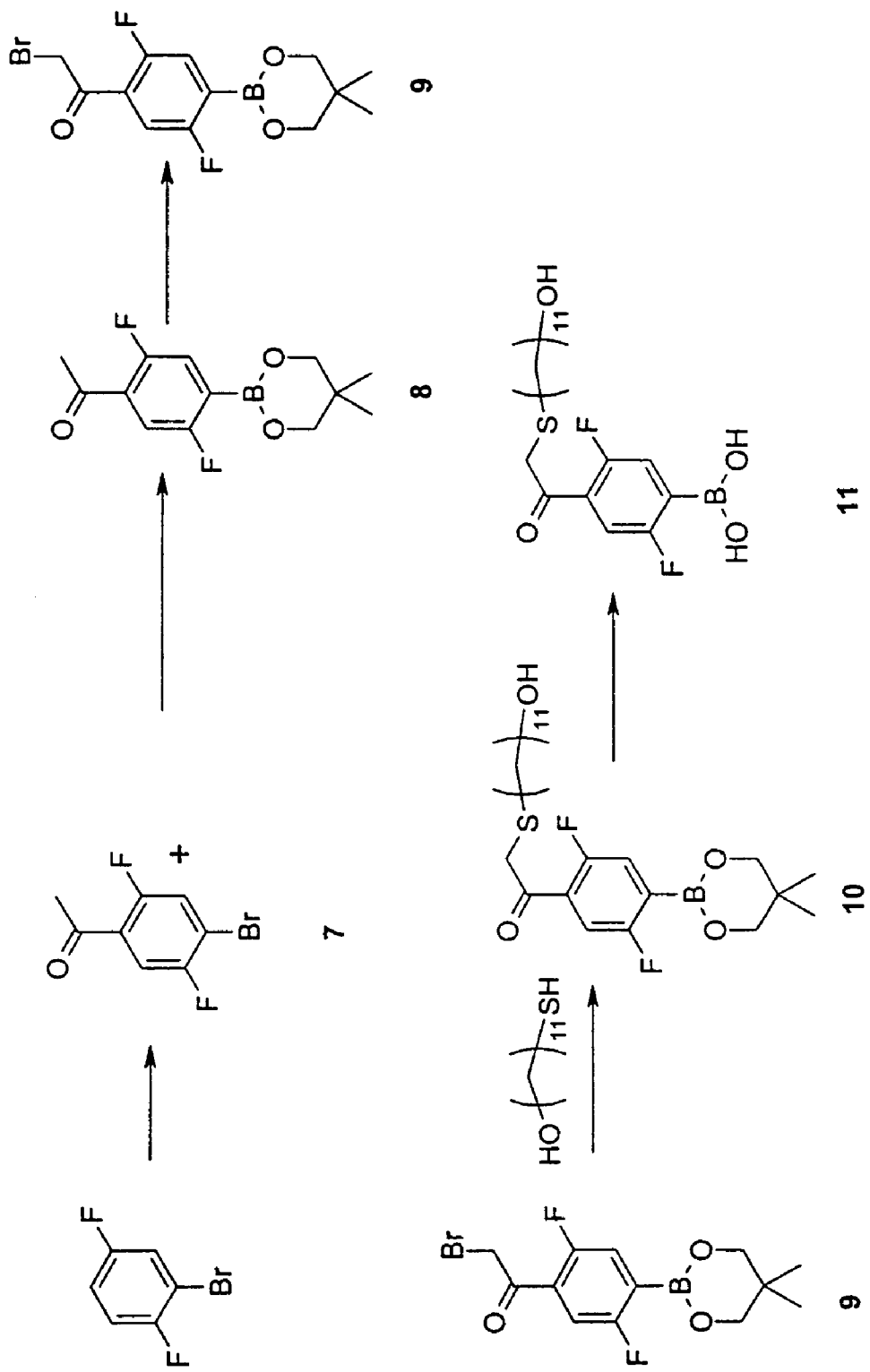
FIG. 2 is a schematic showing the synthesis of 4-(14'-hydroxy-3'-thia-1'-ketotetradecyl)-2,5-difluorophenylboronic acid (11).
Figure 3:
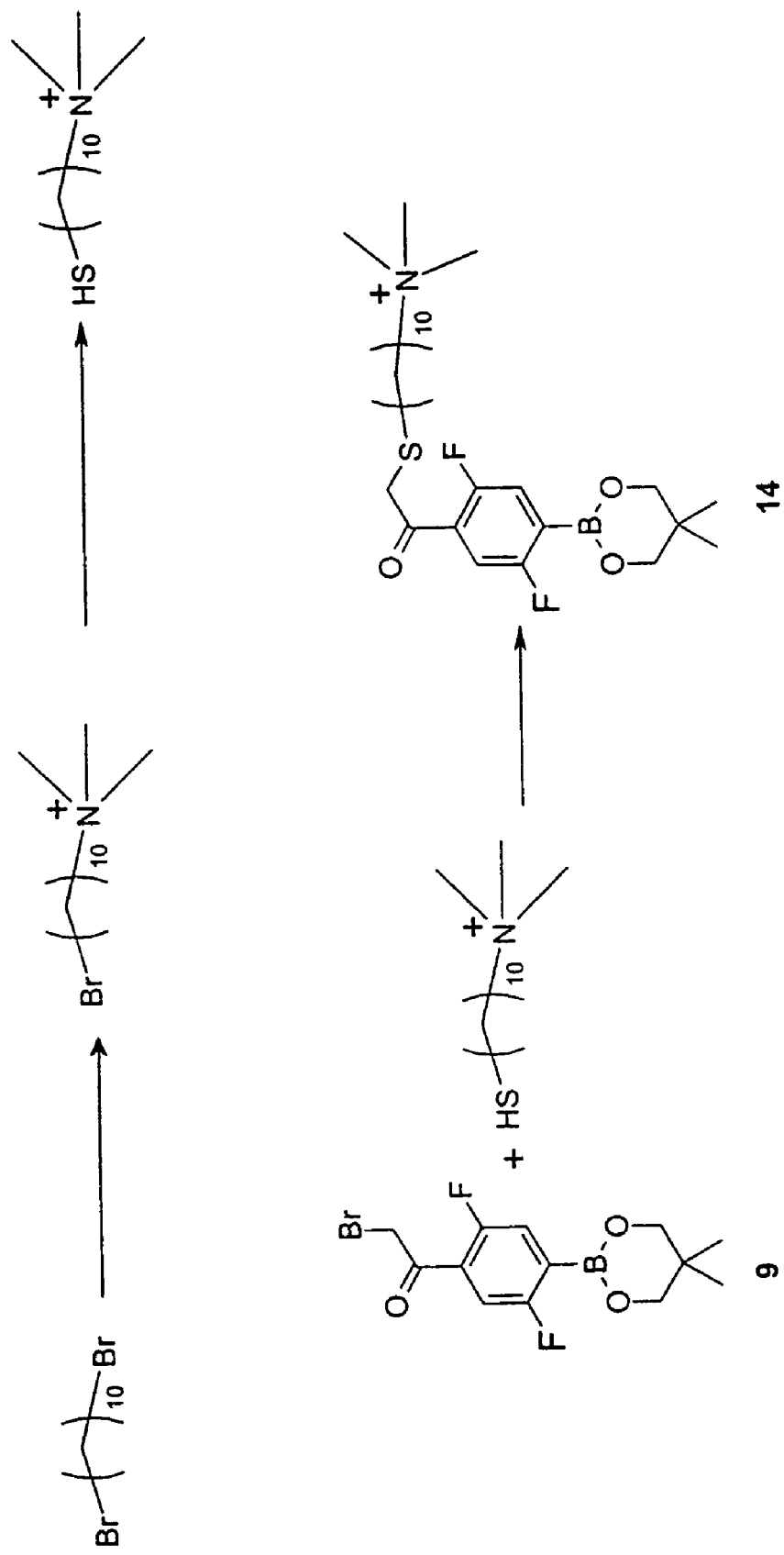
FIG. 3 is a schematic showing the synthesis of (neopentyl glycolato) 4-(14'-trimethylammonium-3'-thia-1'-ketotridecyl)-2,5-difluorophenylboronate ester chloride (14).
Figure 4A:
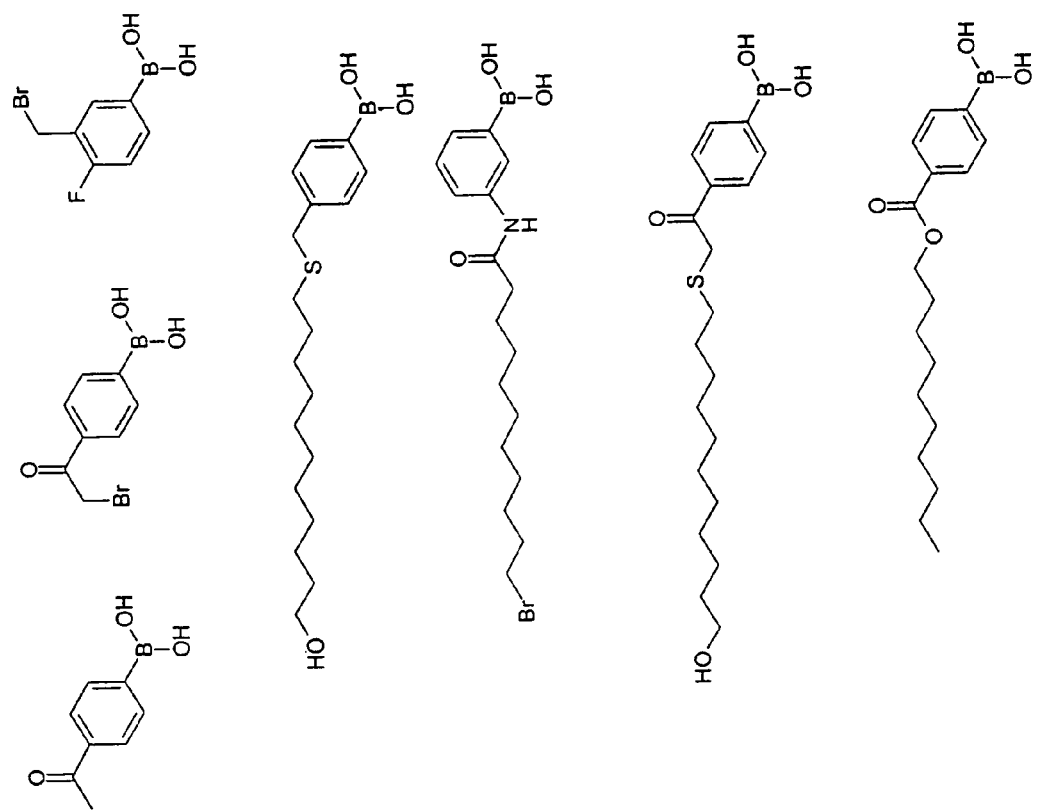
FIGS. 4A–4F are a compilation of structural formulas representing boronic acids of the present invention. R in FIG. 4 is a C12 straight chained alkyl group.
Figure 4B:
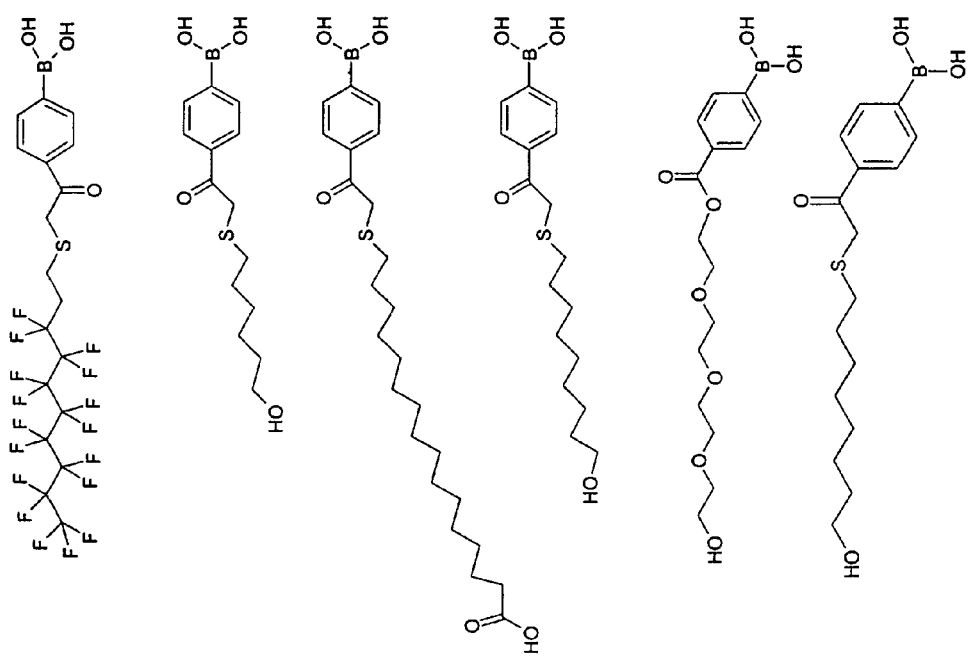
Figure 4C:
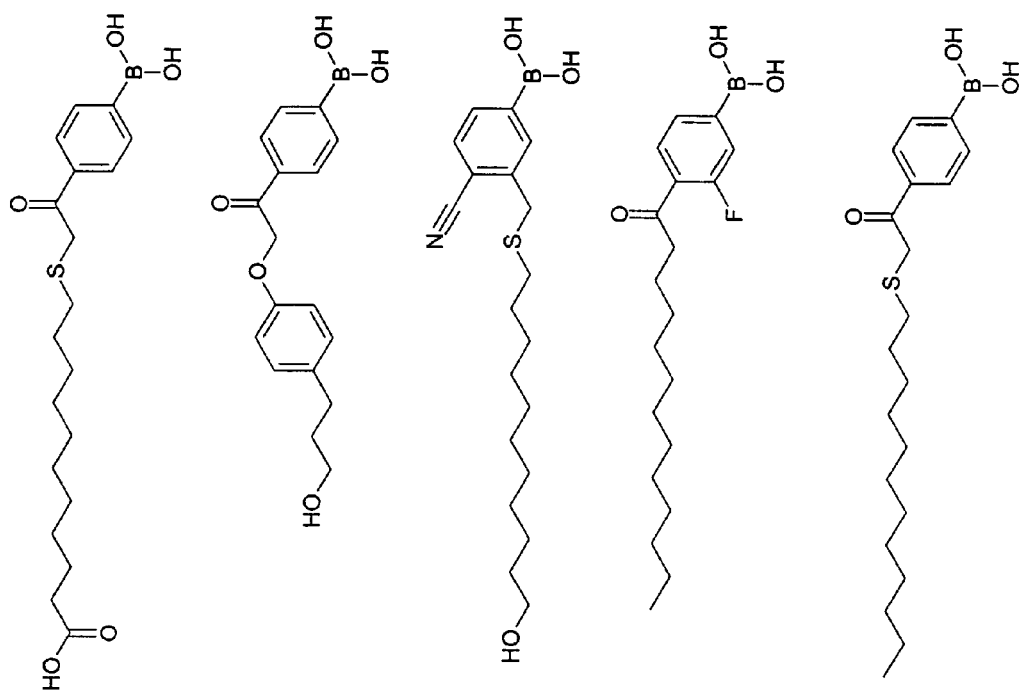
Figure 4D:
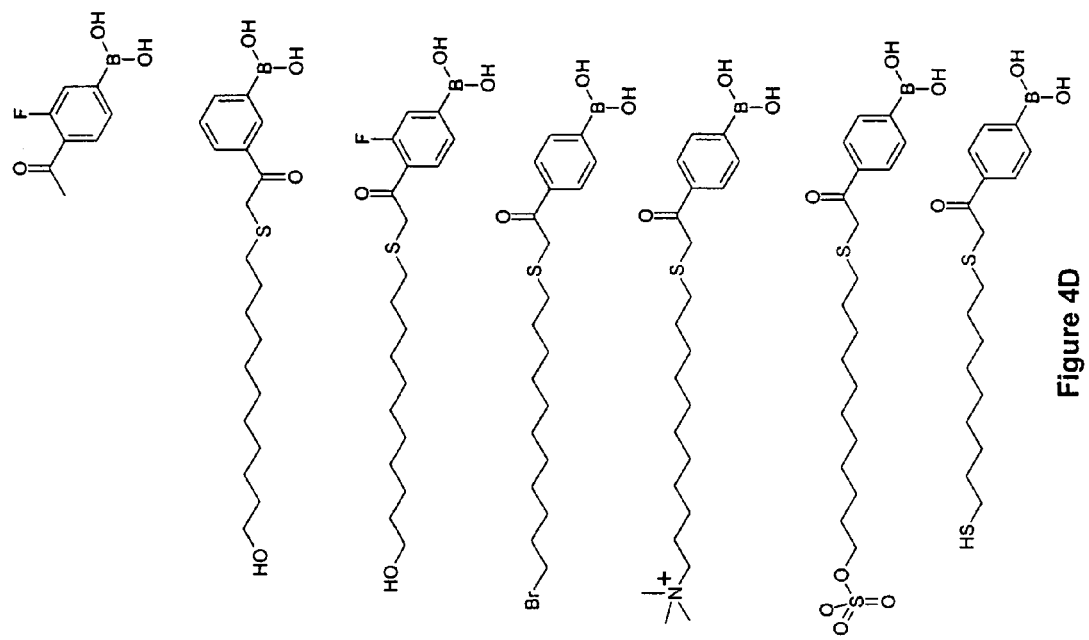
Figure 4E:
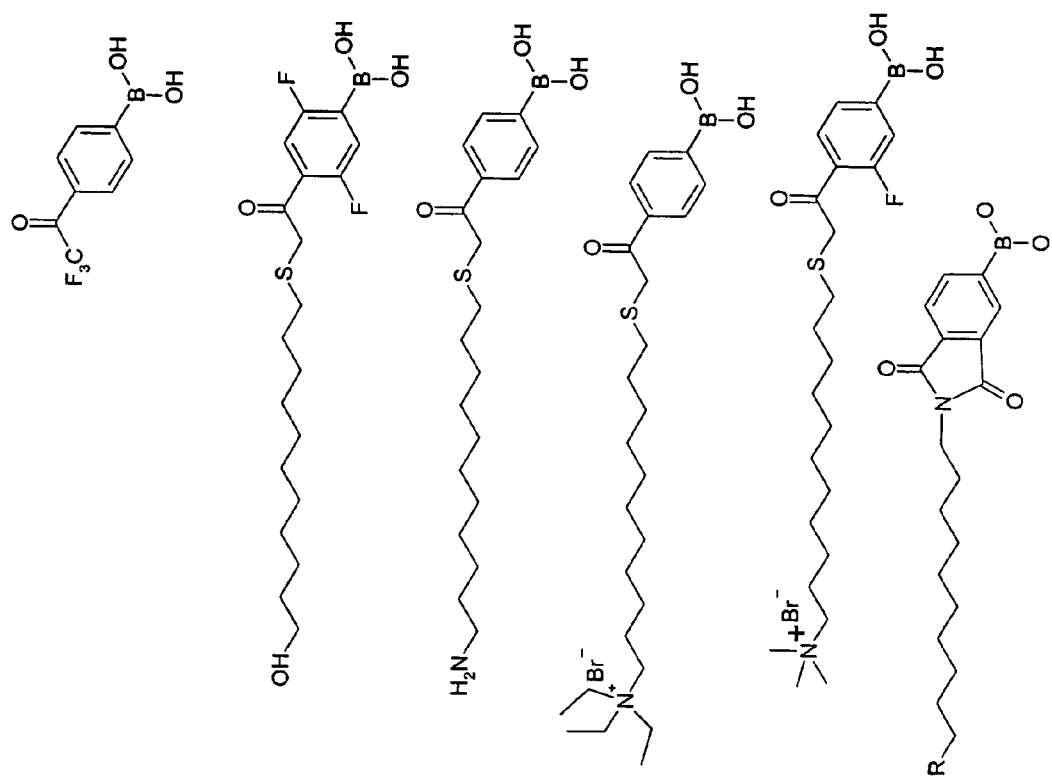
Figure 4F:
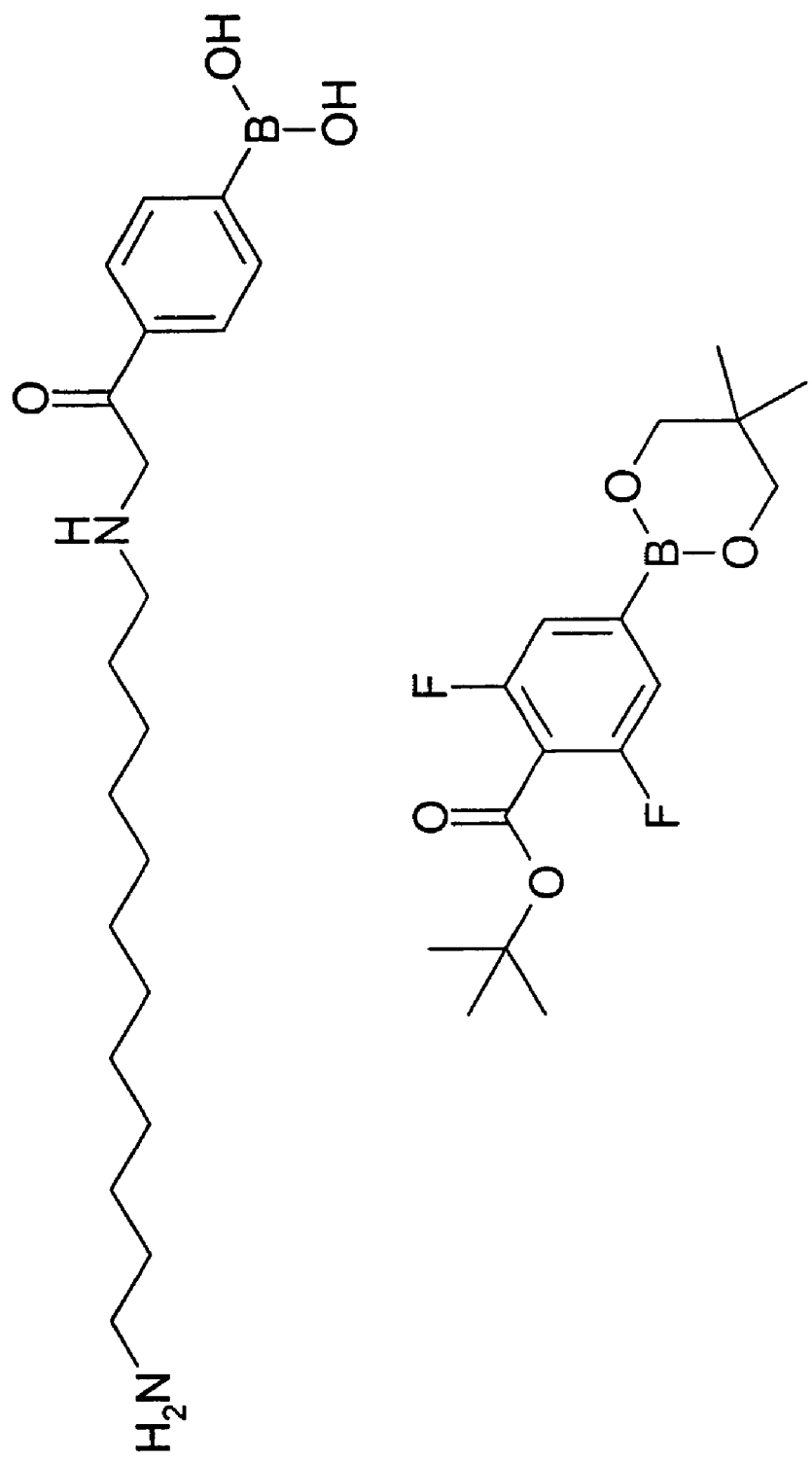

The preparation of representative phenyl boronic acid compounds is described in Examples 1–10 and shown schematically in FIGS. 1–3. The person of ordinary skill in the art will be able to select suitable starting materials to obtain the desired aryl boronic acid and, when carrying out these reactions with different starting materials, to modify reaction conditions, if necessary, using no more than routine experimentation. For example, the 4-bromoacetophenone in FIG. 2 (Compound 7) can be replaced with any suitable aryl compound substituted with bromine or iodine and acetyl. For example, 2-Acetyl-5-bromothiophene is commercially available from the Aldrich Chemical Co., Milwaukee, Wis. The length of the hydrocarbyl group in the aryl boronic acids can be varied according to the length of the 1,ω-alkanethioalcohol.

Representative boronic acids of the present invention that have been prepared according to methods described in the examples are shown in FIG. 4.

The invention is further illustrated by the following examples which is not intended to be limiting in any way.

EXEMPLIFICATION

Example 1

4-(14'-trimethylammonium-3'-thia-1'-ketotetradecyl)-3-fluorophenylboronic acid chloride (6)

The synthesis of Compound (6) is shown out schematically in FIG. 1. A detailed description of the procedure is provided below.

Step 1. Synthesis of 4-acetyl-3-fluorophenylboronic acid (1).

An oven-dried, 3-liter, 3-necked, round-bottomed flask (fitted with a nitrogen inlet, addition funnel, and overhead stirrer) was charged with 50 grams (0.25 mole) of 4-cyano-3-fluorophenyl bromide. Anhydrous tetrahydrofuran (200 milliliters) was added to the flask resulting in a clear solution. The solution was cooled to 0° C. using an ice bath. At this temperature, 125 milliliters of 3.0 M solution of $CH_3MgBr$ in ether (1.5 equivalents, 0.375 mole) was added slowly to the reaction flask using an addition funnel. The reaction mixture was allowed to slowly warm up to room temperature and was stirred for 48 hours. Thin layer chromatography (TLC) indicated the starting material was consumed. After 48 hours, the reaction was cooled down to −78° C. using an isopropanol/dry ice bath. At −78° C., 50 milliliters of 10.0 M solution of butyllithium in hexane (2.0 equivalents, 0.5 mole) was added to the reaction mixture with continuing stirring. An additional 400 milliliters of THF was added to ensure that reaction mixture was homogeneous and was stirring well. The reaction mixture was stirred at −78° C. for 3 hours. To the reaction mixture was added 170 milliliters of trimethylborate (6.0 equivalents, 1.5 mole) slowly using an addition funnel and the temperature was maintained at −78° C. While stirring, the reaction mixture was allowed to warm up to room temperature overnight. The progress of the reaction was monitored by TLC. After cooling the reaction mixture to 0° C. (using an ice bath) the contents were transferred into a 5 liter beaker. The flask was rinsed with 100 milliliters of methanol and the washing was combined with the reaction mixture. To the reaction mixture, 500 milliliters of 1 N HCl was slowly added. Subsequently, the pH of the mixture was brought to 4 by the addition of concentrated HCl. The reaction mixture was stirred for 3 hours. The organic solvent was removed by rotary evaporator. The concentrated aqueous content was extracted with ether (250 milliliter×6). The combined organic layer was washed with brine solution (200 milliliter×2) and was dried over $MgSO_4$. After filtration, ether was removed by rotary evaporator. The residue was recrystallized from hot water yielding an off white solid. Yield: 22 grams (50%).

Step 2. Synthesis of 4-(2'-bromoacetyl)-3-fluorophenylboronic acid (2).

An oven-dried, 500-milliliter, 3-necked, round-bottomed flask was charged with 5 grams (27.4 millimole) of 4-acetyl-3-fluorophenyl boronic acid and 25 milliliters of methanol under a nitrogen atmosphere. The solution was cooled to 0° C. using an ice bath. To this solution was added 0.2 milliliters (0.55 equivalents) of glacial acetic acid. In a 100 milliliters Erlenmeyer flask was taken 1.27 milliliters (3.95 grams, 24 millimole, 0.9 equivalents) of elemental bromine dissolved in 4 milliliters of cold methanol. The bromine solution was added dropwise to the above solution at 0° C. using an addition funnel. With the addition of $Br_2$, the solution slowly turned light orange and finally to dark orange when addition was complete. After about 5–6 hours, the progress of the reaction was monitored by NMR. Depending on the progress of reaction, another 10–20 mole % of bromine was added after cooling the solution to 0° C. Total reaction time was approximately 24 hours.

After completion of the reaction, the solvent was removed using rotary evaporator. The residue was dissolved in 200 milliliters of ethyl acetate. It was washed with deionized water (50 milliliters×3) and with brine (50 milliliters×2). The organic layer was collected and dried over anhydrous sodium sulfate for 1 hour. The solution was filtered and the solvent was removed using rotary evaporator. The residue was recrystallized from hot ethyl acetate. Yield=7 grams (97%).

Step 3. Synthesis of 4-(14'-hydroxy-3'-thia-1'-ketotetradecyl)-3-fluorophenylboronic acid (3).

An oven-dried, 500-milliliter, three-necked, round-bottomed flask was charged with 5 grams (19.15 millimole) of 4-(2'-bromoacetyl)-3-fluorophenylboronic acid (2) and 50 milliliters of anhydrous THF. The solution was flushed with $N_2$ for at least 30 minutes. To this solution was added 3.9 grams (19.15 millimole, 1 equivlalent) of 11-mercaptoundecanol. While stirring under $N_2$, 6.62 milliliters (38.3 millimole, 2 equivalents) of diisopropylethylamine was added slowly. The reaction mixture was stirred at room temperature for 24 hours under nitrogen atmosphere. The progress of the reaction was monitored by TLC and NMR (after washing up the aliquot with 1 N HCl). If the reaction was not complete, additional (as required) 11-mercaptoundecanol was added and the reaction was allowed to proceed for another 24 hours. After completion of the reaction, the solvent was evaporated. The residue was dissolved in 200 milliliters of ethyl acetate and was washed with water (50 milliliters×3), 1 N HCl (50 milliliters×3) and with brine (50 milliliters×2). The organic layer was dried over an anhydrous sodium sulfate for 1 hour. After filtration, the solvent was removed by rotary evaporator. The residue was recrystallized from ethyl acetate. Yield: 5 grams (72%).

Step 4. Synthesis of Neopentyl Glycol Protected 4-(14'-hydroxy-3'-thia-1'-ketotetradecyl)-3-fluorophenylboronic acid (4).

An oven-dried, 500-milliliter, 3-necked, round-bottomed flask was charged with 5 grams (13 millimole) of 3 as prepared above. Addition of 100 milliliters of anhydrous dichloromethane produced a dispersion. While stirring, 1.42 grams (13.65 millimoles, 1.05 equivalents) of neopentylglycol was added to this dispersion. After few minutes a clear solution was obtained. The stirred reaction mixture was heated to reflux. A chiller and a Dean Stark apparatus were used to remove the dichloromethane-water azeotrope. The heating continued for about 3 hours.

At the end of reflux, the reaction mixture was allowed to cool to room temperature and the solvent was removed using a rotary evaporator. Anhydrous toluene (50 milliliters) was added to the residue and the toluene was removed using a rotary evaporator. This toluene treatment process was repeated once more. The residue was dissolved in 5 milliliters of dichlormethane, and hexane was added to this solution (with stirring) until cloudiness appeared (about 150 milliliters). The solution was kept in the freezer for recrystallizaton. After few hours the product crystallized and was isolated by filtration. Yield=5.13 grams (87%).

Step 5. Synthesis of neopentyl glycol protected 4-(14'-bromo-3'-thia-1-ketotetradecyl)-3-fluorophenylboronic acid (5).

The reaction was carried out under $N_2$ atmosphere.

An oven-dried, 500-milliliter, 3-necked, round-bottomed flask was charged with 5.13 grams (11.33 millimole) of the neopentyl glycol protected boronic acid (4) and 50 milliliters of anhydrous dichloromethane under a nitrogen atmosphere. To this solution was added 7.52 grams (22.67 millimole, 2 equivalents) of carbon tetrabromide. The resulting solution was allowed to stir at 0° C. using an ice bath. A solution of 5.95 grams (22.67 millimole, 2 equivalents) of triphenylphosphine dissolved in 10 milliliters of anhydrous dichloromethane was added slowly to the reaction mixture using an addition funnel. The reaction mixture was stirred at 0° C. and was allowed to slowly warm to room temperature. Total reaction time was about 24 hours. At the end of the reaction 20 milliliters of methanol was added to the reaction mixture. After stirring for 1 hour, the solvent was removed by rotary evaporator. The residue was treated with 200 milliliters of diethyl ether and stirred for 30 minutes. The mixture was filtered and the solvent was removed under reduced pressure. The residue was given another ether treatment in the above manner and the solvent was removed. The resulting residue was flash chromatographed using hexane/ethyl acetate (98/2) as the solvent system. After removal of the solvent the product was isolated as an off-white solid. Yield=4.3 grams (74%).

Step 6. Synthesis of 4-(14'-trimethylammonium-3'-thia-1'-ketotetradecyl)-3-fluorophenylboronic acid chloride (6).

A 100-milliliter, round-bottomed flask was charged with 4.3 grams (8.3 millimole) of boronic acid derivative (5) and 40 milliliters of ethanol. To this solution was added 40 milliliters of aqueous trimethylamine solution (40%, Aldrich). The reaction mixture was stirred at 70° C. for 24 hours. After cooling to room temperature, the ethanol was removed by rotary evaporator. The remaining aqueous solution was cooled to 0° C. and 180 milliliters of 1 N HCl was added slowly into the stirring solution. If precipitation occurs, some methanol is added until a clear solution forms. After stirring for 5 hours, the solution (turbid) was extracted with chloroform (3×200 milliliters). Organic layers were collected and dried over sodium sulfate. The chloroform was evaporated and the residue was dissolved in methanol (20 milliliters). Sodium chloride solution (10% w/w, 200 milliliters) was added to the methanol solution and stirred for 1 hour. At this point, the organic solvent was removed using rotary evaporator and compound was extracted from aqueous solution with chloroform (3×200 milliliters). Organic layers were collected and dried over sodium sulfate. After filtration, the solvent was removed using rotary evaporator. The residue was added to 600 milliliters of ether and the mixture was kept in the freezer for 3 hours. The solvent was decanted to isolate the product. Yield=2 grams.

Example 2

Synthesis of 2,5-difluoro-4-(14'-hydroxy-3'-thia-1'-ketotetradecyl)phenylboronic acid (11)

The synthesis of Compound (11) is shown out schematically in FIG. 2. A detailed description of the procedure is provided below.

Step 1—Synthesis of 4-bromo-2,5-difluoroacetophenone (7)

Anhydrous aluminum chloride was mixed (5 grams, 37.5 millimoles, 2.4 equivalents) with 1-bromo-2,5 difluorobenzene in a dry, round-bottom flask blanketed with nitrogen and fitted with a condenser. The mixture was heated to 60° C. and acetyl chloride (1.7 milliliters, 23.3 millimole, 1.5 equivalents) was added by syringe. The wet yellow solid changed then into a scarlet solution and was heated at 90° C. for 1 hour. The reaction mixture was poured onto 38 grams of ice, HCl was added (3 milliliters, 37% concentration) and the mixture was extracted with ether. The crude material was dried over magnesium sulfate and evaporated down. The crude material was purified by column chromatography or distilled. The product (1.2 grams, 31%) was obtained as a yellow oil.

Step 2—Synthesis of Neopentyl Glycol Protected 4-acetyl-2,5-difluorofluorophenylboronic acid (8).

Dichloro [(1,1'-bis(diphenylphosphino)ferrocene]palladium (II) dichloromethane adduct (1.7 grams, 2.3 millimole, 5% mole) was added to a suspension of 4-bromo-2,5 difluoroacetophenone (7) (10.5 grams, 46.38 millimole, 1 equivalents), bis(neopentyl glycolato)diboron (12.57 grams, 55.65 millimole, 1.2 equivalents) and potassium acetate (13.66 grams, 139.13 millimole, 3 equivalents) in anhydrous DMSO (100 milliliters). The suspension was heated to 80° C. under nitrogen for 1 hour (*J. Org. Chem.* 60:7508 (1995)). After 1 hour, TLC showed full conversion of the starting material and the reaction mixture was allowed to cool down and extracted with toluene, washed three times with water and dried over magnesium sulfate. Flash column chromatography was used to purify the crude (4.2 grams, 32%).

Step 3—Synthesis of Neopentyl Glycol Protected 4-(2'-bromoacetyl)-2,5-difluorophenylboronic acid (9)

The boronic ester (8) (4.1 grams, 14.93 millimole, 1 equivalent) was dissolved in methylene chloride (50 milliliters) and cooled down to −10° C. Acetic acid (0.82 milliliters, 14.32 millimole, 1 equivalent) was added, followed by bromine (0.7 milliliters, 13.4 millimole, 0.9 equivalents) and the reaction was warmed up to room temperature. After stirring for two hours the reaction mixture was diluted with more methylene chloride and washed once with water and once with brine. The crude was dried over magnesium sulfate, evaporated down and used in the next step without further purification.

Step 4—Synthesis of Neopentyl Glycol Protected 2,5-difluoro-4-(14'-hydroxy-3'-thia-1'-ketotetradecyl)phenylboronic acid (10)

Crude Compound (9) (14.93 millimole) was dissolved in anhydrous methanol (50 milliliters) and nitrogen gas was bubbled into the solution for 20 minutes to degas the mixture. 11-mercaptoundecanol (3.1 grams, 14.93 millimole, 1 equivalent) was added to the reaction and the solution was allowed to stir under nitrogen for five minutes before adding anhydrous diisopropylamine (5.2 milliliters, 29.9 millimole, 2 equivalents). The reaction was left to stir under nitrogen overnight and the crude was worked up by evaporating the reaction mixture to dryness and re-dissolving it in a 10% mixture of THF in ethyl acetate (100 milliliters). This organic layer was then washed with 200 milliliters of water and the aqueous layer was separated and washed with three new fractions of the same THF/ethyl acetate mixture (100 milliliters each). The crude organic layers were combined, dried over magnesium sulfate and evaporated down. Flash chromatography was used to purify the crude and an off white solid was obtained (3.5 grams, 50%).

Step 5—Synthesis of 2,5-difluoro-4-(14'-hydroxy-3'-thia-1'-ketotetradecyl)phenylboronic acid (11).

De-protection of the neopentyl group in Compound (10) to give Compound (11) was carried out by dissolving Compound (10) in methanol and adding a few drops of HCl. After stirring for about an hour the crude product was concentrated on a rotary evaporator and the final compound was recrystallized from hot ethyl acetate.

Example 3

Synthesis of 2,5-difluoro-4-(13'-trimethylamonium-3'-thia-1'-ketotridecyl)phenyl(neopentyl glycolato) boron chloride (14)

The synthesis of Compound (14) is shown schematically in FIG. 3. A detailed description of the procedure is provided below.

Step 1—Synthesis of 10-bromodecyltrimethylammonium bromide 1,10-Dibromodecane (20 grams, 66.7 mmoles) and THF (100 milliliters) were placed in a 500-mL, three-necked flask. The solution was cooled to 0° C. with an ice-water bath. Anhydrous trimethylamine (3 grams, 50.8 mmoles) was added to the mixture by slowly bubbling trimethylamine gas for about 15 minutes. Then the reaction mixture was allowed to warm to room temperature and stirred at room temperature overnight. The solid material was filtered and washed with THF (5×30 milliliters). After drying in vacuo overnight, 12.5 grams (34.82 mmoles, 69% based on the amine used) of the product was obtained as a white solid.

Step 2—Synthesis of 10-mercaptodecy trimethylammonium bromide

10-Bromodecyltrimethylammonium bromide (10 grams, 27.9 mmoles) in 50 mL of methanol was placed in a 250-milliliter, three-necked flask. The mixture was degassed vigorously by bubbling nitrogen for 30 min. Potassium thioacetate (3.8 grams, 33.5 mmoles, 1.2 equivalents) was added to the reaction mixture. The mixture was heated at 50° C. for 12 hours under nitrogen. The reaction mixture was cooled to 0° C. with an ice-water bath, degassed sodium hydroxide (50%, 2.7 grams, 33.5 mmoles, 1.2 equivalents) was added, and the mixture was stirred for 1 h at room temperature. The mixture was cooled to 0° C., and degassed concentrated hydrochloride acid was added dropwise to achieve pH 2. Degassed methanol (100 milliliters) was added to the reaction mixture, followed by the addition of 40 grams of magnesium sulfate. Magnesium sulfate was filtered off and washed with methanol. The methanol solution was concentrated to about 20 milliliters, and ether (300 milliliters) was added to the mixture. The flask was sealed and placed in a freezer. Product was crystallized out as a white solid. The product was filtered, washed with ether, and dried in vacuo. Product (7.5 grams, 24.0 mmoles, 86%) was obtained as a white hydroscopic solid.

Step 3—Synthesis of 2,5-difluoro-4-(13'-trimethylammonium-3'-thia-1'-ketotridecyl)fluorophenylboronic acid bromide 4-(2'-Bromoacetyl)-2,5-difluorophenyl (neopentyl glycolato) boron (Compound 9) (1 millimole) was dissolved in anhydrous methanol (10 milliliters) and nitrogen gas was bubbled into the solution for 20 minutes to degas the mixture. 10-mercaptodecyltrimethylammonium bromide (0.19 grams, 0.8 millimole, 0.8 equivalents) was added to the reaction and the solution was stirred under nitrogen for five minutes before adding anhydrous diisopropylamine (0.14 milliliters, 1 millimole, 1 equivalent). The reaction was stirred under nitrogen overnight and, after concentration on a rotary evaporator, purified by preparative reversed phase PLC.

Example 4

Synthesis of 4-(14'-trimethylammonium-3'-thia-1'-keto-tetradecyl)phenylboronic acid chloride Step 1. Synthesis of 4-(2'-Bromoacetyl)phenylboronic acid.

An oven-dried, two liter, three-necked, round-bottomed flask was charged with 4-acetyl-phenylboronic acid (20 grams, 0.152 mole). While stirring, 175 ml of THF were added to the reaction mixture, followed by 700 ml of chloroform. To the resulting solution was added 5 ml of glacial acetic acid. A chloroform solution of bromine (prepared by dissolving 7 ml of bromine in 30 ml of chloroform) was added slowly to the reaction mixture at about 5° C. After the completion of the addition of bromine, the reaction mixture was allowed to warm to room temperature and stirred at room temperature for 16 hours. The solvent was removed by rotary evaporation and the residue was dissolved in 1 liter of ethyl acetate. The resulting solution was extracted with deionized water (3×200 ml) and brine (2×100 ml). The organic layer was dried over anhydrous sodium sulfate for 1 hour. The solution was then filtered and concentrated to about ⅓ of its volume. The resulting solution was kept in a freezer to crystallize the product. The solid was filtered to give an off white solid. Yield=16 grams Step 2. 4-(14'-hydroxy-3'-thia-1'-ketotetradecyl)phenylboronic acid.

A 500-ml, three-necked, round-bottomed flask was charged with 15 grams of 4-(2'-bromoacetyl)phenylboronic acid and 300 ml of anhydrous THF. While stirring under a nitrogen atmosphere, 12.26 grams of 11-mercaptoundecanol were added to the reaction mixture, followed by 32.35 ml of diisopropylethylamine. The reaction mixture was stirred under a nitrogen atmosphere for 48 hours. After removing the solvent by rotary evaporation, the residue was dissolved in 500 ml of ethyl acetate. The organic phase was washed with deionized water (2×200 ml), 1N HCl (3×200 ml), deionized water (200 ml), and brine (200 ml). The washed organic layer was then dried over anhydrous sodium sulfate for 15 minutes. The solution was filtered and concentrated to one fourth of its volume. While stirring, hexane was added slowly to this solution until permanent cloudiness appeared. The solution was kept in the freezer to crystallize the product. After filtration, the residue was dried under vacuum at room temperature yielding 17 grams of the product as an off-white solid.

Step 3. Synthesis of (neopentyl glycolato)4-(14'-hydroxy-3'-thia-1'-ketotetradecyl)phenylboronate ester.

An oven-dried, 500 ml, 3-necked, round-bottomed, flask was charged with 5 grams of 4-(14'-hydroxy-3-thia-1-keto) tetradecyl phenylboronic acid and 100 ml of anhydrous dichloromethane. While stirring, 1 gram of neopentylglycol was added and the reaction mixture was heated to reflux with stirring. The heating continued for 3 hours with azeotropic distillation of water. The reaction mixture was allowed to cool to room temperature and the solvent was removed using a rotary evaporator. Anhydrous toluene (50 ml) was added to the residue and the toluene was removed using a rotary evaporator. This toluene treatment process was repeated once more. The residue was dissolved in 5 ml of dichloromethane and hexane was added to this solution (with stirring) until cloudiness appeared. The solution was kept in the freezer for recrystallizaton. The product was isolated by

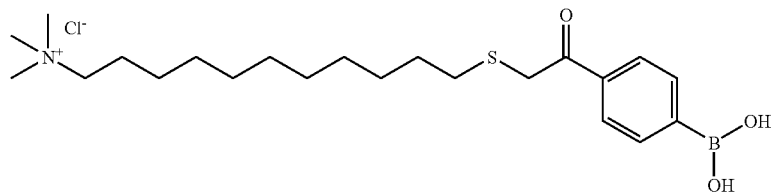

filtration, and upon drying, 4.8 grams of the compound was obtained as an off-white solid.

Step 4. Synthesis of (neopentyl glycolato)4-(14'-bromo-3'-thia-1'-ketotetradecyl) phenylboronate ester.

An oven-dried, 500 ml, 3-necked, round-bottomed flask was charged with 5.13 grams of the (neopentyl glycolato) 4-(14'-hydroxy-3'-thia-1'-ketotetradecyl)phenylboronate ester and 50 ml of anhydrous dichloromethane. To this solution was added 7.52 grams of carbontetrabromide, and the resulting reaction mixture was allowed to stir at 0° C. using an ice bath. A solution of 5.95 grams of triphenylphosphine dissolved in 10 ml of anhydrous dichloromethane was added slowly to the reaction mixture using an addition funnel. The reaction mixture was stirred at 0° C. and then allowed to warm to room temperature slowly. After 16 hours, 20 ml of methanol was added to the reaction mixture. After stirring for 1 hour, the solvent was removed by rotary evaporator. The residue was treated with 200 ml of diethyl ether and stirred for 30 minutes. The mixture was filtered and the solvent was removed under reduced pressure. The residue was again treated with ether and the solvent was removed. The resulting residue was flash chromatographed using hexane/ethyl acetate (98/2). After removal of the solvent, the product was isolated as an off-white solid (yield=4.5 grams).

Step 5. 4-(14'-trimethylammonium-3'-thia-1'-keto-tetradecyl)phenylboronic acid chloride.

A 100 ml, round-bottomed, flask was charged with 500 mg of (neopentyl glycolato)4-(14'-bromo-3'-thia-1'-ketotetradecyl)phenylboronate ester and 5 ml of ethanol. To this solution was added 5 ml of 40% aqueous solution of trimethylamine. The reaction mixture was stirred at 70° C. for 24 hours. After cooling to room temperature, the solvent was removed under reduced pressure. The residue was dissolved in 5 ml of methanol and 20 ml 2N HCl. After stirring for 24 hours, the solution was extracted with ethyl acetate (2×100 ml) to remove the neopentyl glycol. The aqueous solution was extracted with chloroform (3×50 ml). The chloroform extracts were combined and dried over $MgSO_4$. After filtration, the solvent was removed under reduced pressure and the residue was dried under vacuum to give 300 mg of a gummy solid.

Example 5

Synthesis of (neopentyl glycolato)4-(14'-dimethylamino-3'-thia-1'-ketotetradecyl)phenylboronate ester

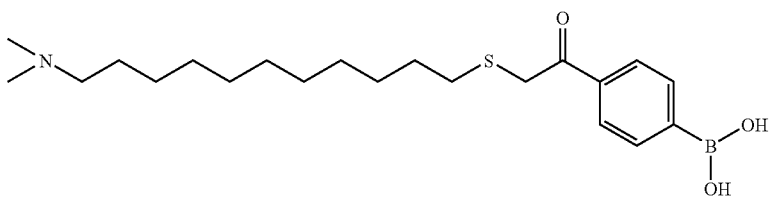

An oven-dried, 250 ml, 3-necked, round-bottomed flask was charged with 2.5 grams of the (neopentyl glycolato)4-(14'-bromo-3'-thia-1'-keto)tetradecyl phenylboronate ester (prepared as described in Example 4, step 4) and 25 ml of anhydrous tetrahydrofuran (THF). To this mixture was added 8 ml of 2 M dimethylamine in THF. After stirring at room temperature for 48 hours, the solvent was removed under reduced pressure. The residue was stirred with 100 ml of 5% aqueous sodium bicarbonate solution for 1 hour and was then extracted with ethyl acetate (2×200 ml). After drying over anhydrous sodium sulfate, the solvent was removed under reduced pressure to yield 1.7 grams of the compound as a gummy solid.

Example 6

Synthesis of 4-{14'(3"-chlorotrimethylammium) dimethylpropylammonium-3'-thia-1'-ketotetradecyl}phenylboronic Acid Chloride

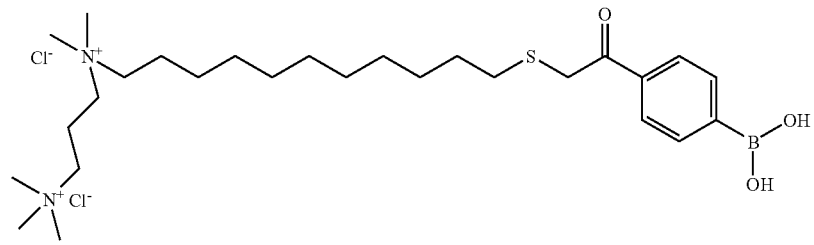

A 100 ml, round-bottomed, flask was charged with 700 mg of (neopentyl glycolato)4-(14'-dimethylamino-3'-thia-1'-ketotetradecyl)phenylboronate ester (prepared as described in Example 5), 400 mg of 3-bromopropyltrimethylammonium bromide and 10 ml of ethanol. The reaction mixture was stirred at 70° C. for 24 hours. After cooling to room temperature, the solvent was removed under reduced pressure. The residue was dissolved in 5 ml of methanol and 40 ml 2 N HCl. After stirring for 24 hours, the solution was extracted with ethyl acetate (2×100 ml) to remove neopentyl glycol. The acidified aqueous solution was kept in the refrigerator. The precipitated solid was then isolated by removal of the solvent and dried under vacuum to yield 400 mg of a low melting solid.

Example 7

Synthesis of 4-(14'-sulfato-3'-thia-1'-ketotetradecyl) phenylboronic acid sodium salt

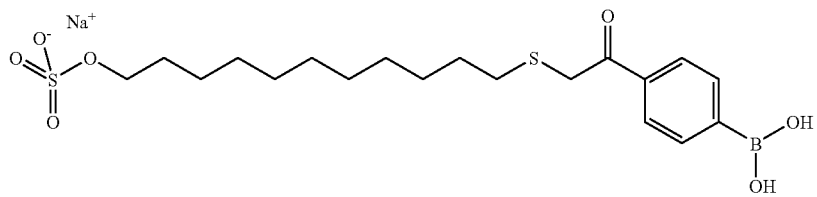

A 100 ml, round-bottomed flask was charged with 3 grams of 4-(14'-hydroxy-3'-thia-1'-ketotetradecyl)phenylboronic acid (prepared as described in Example 4, step 2) and 25 ml of N,N-dimethylformamide (DMF). To this solution was added 1.6 grams of sulfurtrioxide:DMF complex and the resulting reaction mixture was stirred at room temperature for 24 hours. To the reaction mixture was added a solution 2 grams of NaOH dissolved in 100 ml of water:methanol mixture (1:1) and stirred for 1 hour. The solvent was removed under pressure and the residue was treated with 100 ml of methanol. After stirring for 1 hour, the reaction mixture was filtered. The filtrate was rotary evaporated to dryness, yielding 1.5 grams of an off-white solid.

Example 8

Preparation of 4-(11'-hydroxyundecyl)carboxyphenylboronic acid

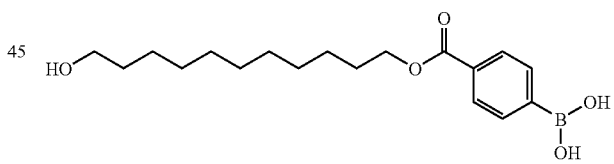

A mixture of 4-carboxyphenylboronic acid (1.0 grams), potassium hydrogen carbonate (2.01 g), 11-bromo-1-undecanol, and N,N-dimethylformamide (60 mL) was heated at 60° C. under a nitrogen atmosphere for 18 hours. After the heating period, the mixture was allowed to cool to room temperature. The mixture was then filtered and the filtrate was concentrated on a rotary evaporator. The concentrated filtrate was diluted with ethyl acetate (500 mL) and the ethyl acetate was washed successively with saturated aqueous sodium bicarbonate (3×300 mL), followed by saturated aqueous sodium chloride (300 mL). After drying over sodium sulfate, the ethyl acetate extract was concentrated on a rotary evaporator and dried under reduced pressure to afford 2.2 grams of the desired product as a light yellow viscous oil that solidified upon standing to a white powder.

The following compounds were synthesized using similar procedures:

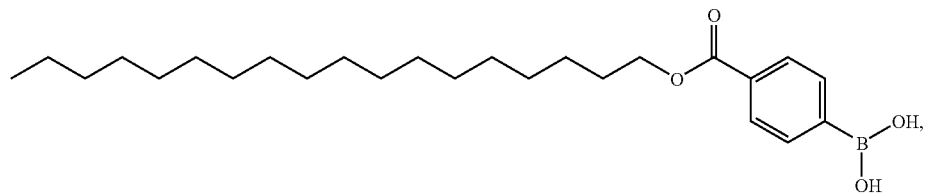
from 4-carboxyphenylboronic acid and iodooctadecane;
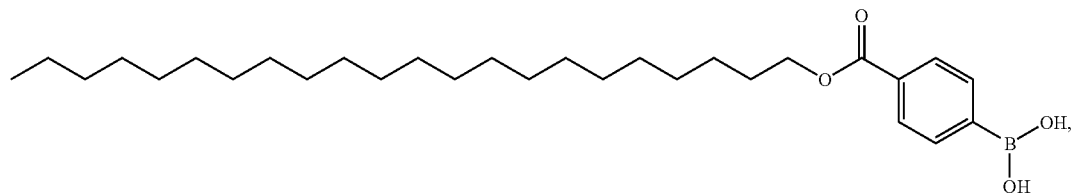
from 4-carboxyphenylboronic acid and docosyl methane sulfonate;
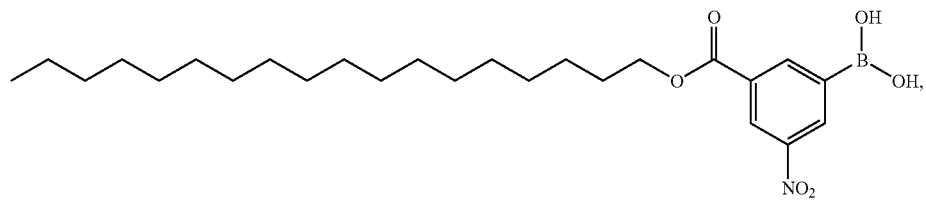
from bromooctadecane and (3-carboxy-5-nitrophenyl)boronic acid;
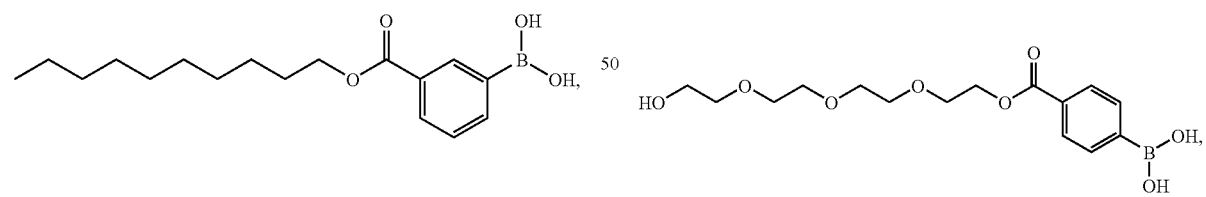
from 1-bromodecane and (3-carboxyphenyl)boronic acid;
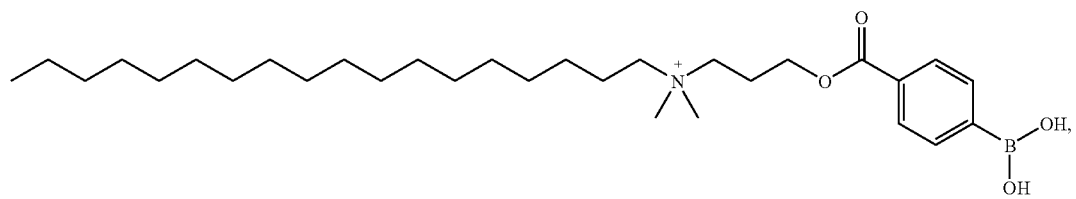
from 4-carboxyphenylboronic acid and (4-chloropropyl)dimethyloctadecylammonium bromide; and

21 from 4-carboxyphenylboronic acid and pentethyleneglycol monotosylate.

Example 9

Synthesis of [4-(N,N-dioctadecylcarbamoyl)phenyl]boronic acid

Step 1. Synthesis of 2-(4-carboxyphenyl)-1,3-dioxa-2-borinane.

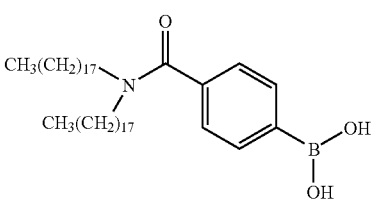

A mixture of 4-carboxyphenylboronic acid (5.0 grams) and 1,3-propanediol (2.5 grams) in toluene (300 mL) was refluxed with a Dean-Stark apparatus for 6 hours. After the heating period the reaction solution was concentrated on a rotary evaporator and dried under reduced pressure to afford 6.39 grams of the desired product as a white solid.

Step 2. Synthesis of 2-(4-carbonylchloride)-1,3-dioxa-2-borinane.

To a solution of the above propane diol protected 4-carboxyphenylboronic acid (1.0 grams) in chloroform (5 mL) was added thionyl chloride (3.0 mL) and dimethylformamide (100 microliters). The solution was heated to reflux for 2 hours. After the heating period, the reaction solution was allowed to cool to room temperature and was concentrated on a rotary evaporator under reduced pressure. To the residue was added chloroform (8 mL) and the resulting solution was concentrated on a rotary evaporator. The addition of chloroform (8 mL) and the concentrating of the solution was repeated twice more. The crude material was dried under vacuum to afford 1.09 grams of the desired product as an off-white solid.

Step 3. Synthesis of [4-(N,N-dioctadecylcarbamoyl)phenyl]boronic acid.

To a solution of 2-(4-carbonylchloride)-1,3-dioxa-2-borinane (0.8 grams) in chloroform (30 mL) under nitrogen was added dioctadecylamine (1.93 grams), triethylamine (1.0 mL), and chloroform (10 mL). The reaction mixture was allowed to stir overnight, after which it was diluted with chloroform (200 mL). The chloroform solution was washed in a separatory funnel successively with the following aqueous solutions: 10% HCl (3×100 mL), saturated sodium bicarbonate (3×100 mL), and saturated sodium chloride (100 mL). The chloroform extract was dried over sodium sulfate. 2.41 grams of crude material was isolated after filtration and concentration on a rotary evaporator under reduced pressure. The desired product was purified via column chromatography over silica gel using a mixture of ethyl acetate and hexane as eluent.

Example 10

Synthesis of 4-(13'-carboxy-3'-thia-1'-ketotridecyl)phenylboronic acid

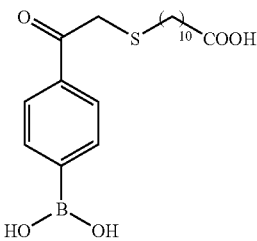

A 100-mL, three-necked flask was charged with 4-(2'-bromoacetyl)phenyl boronic acid (0.95 g, 3.91 mmol) and 20 mL THF. The mixture was degassed by bubbling nitrogen through the reaction mixture for about 20 minutes. 11-Mercaptoundecanoic acid (0.9 g, 4.1 mmol) was added to the reaction mixture with stirring under nitrogen. Diisopropylethylamine (1.52 g, 2.05 mL, 11.8 mmol) was then added via a syringe over 5 minutes. The reaction mixture was stirred for 72 hours under nitrogen at room temperature. The solvent was removed in vacuo, and the residue was partitioned between ethyl acetate (100 mL) and water (100 mL). The organic extract was washed with 1 N hydrochloric acid (3×100 mL), water (100 mL) and brine (100 mL). The organic extract was dried over magnesium sulfate and then filtered. The filtrate was then concentrated in vacuo. The residue was dissolved in about 25 mL of hot ethyl acetate. When the mixture was cooled to room temperature, it was placed in a freezer. Product crystallized from the solution. The white crystalline material was filtered, washed with cold ethyl acetate, and dried in vacuo. 0.93 g (2.45 mmol) of the pure product was obtained. Yield: 62.5%.

Example 11

Phenyl Boronic Acids of the Present Invention Inhibit Lipolysis In Vitro

An in vitro assay of pancreatic lipase activity was used to measure the efficacy of lipase inhibitory compounds. Porcine pancreatic lipase (23 units/milliliters) was incubated for 4 hours at 37° C. with 72 mM triglyceride (as an olive oil/gum arabic emulsion) in 5.5 milliliters of a 300 mM BES buffer, pH 7.0, containing 10 mM $CaCl_2$, 109 mM NaCl, and 8 mM sodium taurocholate. The reaction was stopped by acidification with HCl and the lipids were extracted by the method disclosed in Folch, et al., J. Biol. Chem. 226:497 (1957) prior to analysis by HPLC. An aliquot of the chloroform layer was evaporated and reconstituted in hexane, and the sample was analyzed on a Waters Alliance 2690 HPLC with a Sedex 55 Evaporative Light Scattering detector utilizing a YMC PVA Sil 3×50 millimeter column. The mobile phase consisted of hexane and methyl t-butyl ether delivered in a linear gradient at a flow rate of 0.5 milliliters/ minute. External standards were utilized for quantitation of triglycerides, diglycerides, and fatty acids, and the percent lipolysis was determined. For evaluation of lipase inhibitor efficacy, compounds were dissolved in DMSO or another appropriate solvent and added directly to the assay mixture prior to incubation. Inhibition was determined relative to a control incubation and $IC_{50}$ values were calculated from a plot of % inhibition vs. inhibitor concentration. The results are shown in the Table. As can be seen, the boronic acid compounds of the present invention are effective lipase inhibitors.

Example 12

Phenyl Boronic Acids of the Present Invention Inhibit Lipolysis In Vivo

Compounds were evaluated in rats to determine their in vivo potency in inhibiting fat absorption through lipase inhibition. Rats were acclimated to the facility for approximately 1 week in individual wire-bottom cages and provided a standard chow diet and water ad libitum. Rats were then randomly assigned to groups of 4. They were gavaged at (7–8 AM) with 4 milliliters olive oil emulsified with gum arabic, with or without drug following an 18 hour fast. Test compounds were dissolved in DMSO or dionized water. Drug solutions were mixed thoroughly in the olive oil emulsion just prior to administration. After 8 hours, rats were euthanized with $CO_2$ and the intestines were removed. The intestinal contents were harvested from the lower half of the small intestine and the cecum. Contents were placed in separate, pre-weighed, 15 milliliters conical screw cap tubes in a (dry ice/alcohol bath) to maintain freezing temperature until the final freeze of all samples. Samples were stored at −80° C. until lyophilization.

Samples were freeze-dried and ground, then analyzed for triglyceride and fatty acid.

A 20 milligrams aliquot of each sample was weighed and transferred to a 15 milliliters conical tube. 3 milliliters of hexane was added to each tube then it was capped and vortexed for 15 seconds at high speed. 3 milliliters of 1 N HCl was added then samples were subjected to wrist-action shaking for 1 hour. Samples were then centrifuged for 5 minutes at 3500 rpm and the hexane layer was collected. An aliquot of the hexane layer was diluted in hexane and analyzed for triglyceride, diglyceride and fatty acid by HPLC as described above.

The data was expressed as follows. The milligrams of intestinal contents that were extracted and the total number of milligrams collected were recorded. The milligrams/milliliters values obtained from the HPLC analysis were entered. The individual lipid components were calculated and expressed as total milligrams recovered. Dose units are expressed as the milligrams of drug per gram of oil administered to each rat. The $ED_{50}$'s were determined by extrapolating the dose value at half the maximum obtainable triglyceride recoverable in the assay. The results are shown in the Table. As can be seen, the boronic acid compounds of the present invention are effective lipase inhibitors in vivo.

TABLE

Inhibition of in vitro and in vivo lipolysis

| Test Compound | In Vitro Pancreatic Lipase Assay $IC_{50}$ (µg/g fat) or estimate | In Vivo Infusion Assay in Rats $ED_{50}$ (mg/g fat) or estimate | In Vivo Infusion Assay in Rats $Ed_{50}$ (mg/kg body wt) or estimate |
|---|---|---|---|
| 4-(14'-trimethylammonium-3'-thia-1'-keto-tetradecyl)-phenyl-boronic acid bromide | 6.4 | 8 | 60 |
| 4-(14'-trimethylammonium-3'-thia-1'-keto-tridecyl)-3-fluorophenyl-boronic acid bromide | 1.8 | 2 | 15 |
| 4-(14'-triethylainmonium-3'-thia-1'-keto-tetradecyl)-3-phenyl-boronic acid bromide | 11 | 11 | 82.5 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a subject afflicted with a condition selected from the group consisting of Type II diabetes mellitus, impaired glucose tolerance, hypertension, coronary thrombosis, stroke, lipid syndromes, hyperglycemia, hypertriglyceridemia, hyperlipidemia, sleep apnea, hiatal hernia, reflux esophagisitis, osteoarthritis, gout, gallstones, kidney stones, pulmonary hypertension, infertility and cardiovascular disease, the method comprising the step of administering to the subject an effective amount of a compound represented by the following structural formula:

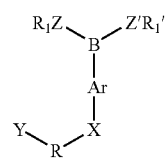

or a pharmaceutically acceptable salt thereof, wherein:
  Z and Z' are independently —O—, —NH— or —S—;
  Ar is a substituted or unsubstituted aryl group;
  X is an electron withdrawing group;
  R is a substituted or unsubstituted straight chained hydrocarbyl group optionally comprising one or more amine, ammonium, ether, thioether or phenylene linking groups;
  Y is —H, an amine, —[NH—$(CH_2)_q$]$_r$—$NH_2$, halogen, —$CF_3$, thiol, ammonium, —OH, —COOH, —$SO_3H$, —$OSO_3H$ or phosphonium group covalently bonded to the terminal position of R, provided that when Y is —H and R is a straight chained hydrocarbyl group, then R has from 1 to 30 carbon atoms, and provided that each —NH— in —[NH—$(CH_2)_q$]$_r$—$NH_2$ is optionally N-alkylated or N,N-dialkylated and —$NH_2$ in —[NH—$(CH_2)_q$]$_r$—$NH_2$ is optionally N-alkylated, N,N-dialkylated or N,N,N-trialkylated;
  q is an integer from 2 to about 10;

r is an integer from 1 to about 5;

$R_1$ and $R_1'$ are independently —H, an aliphatic group, a substituted aliphatic group, an aryl group or a substituted aryl group or, taken together, are a C2–C5 substituted or unsubstituted alkylene group optionally comprising an amine linking group [—$N^+(R^{1a})$—]; and $R^{1a}$ is —H, alkyl, substituted alkyl, phenyl or substituted phenyl.

2. The method of claim 1 provided that when Y is —H and R is a straight chained hydrocarbyl group, then R has from 4 to 30 carbon atoms.

3. The method of claim 2 wherein Z and Z' are both —O—.

4. The method of claim 3 wherein Ar is a substituted or unsubstituted phenyl group.

5. The method of claim 4 wherein $R_1$ and $R_1'$ are both —H.

6. The method of claim 5 wherein X is —$CZ''_2$—, —$CHZ''$—, —COO—, —$CONR^{1b}$—, —CO—, —S(O)—, —$S(O)_2O$— or —$SO_2$—; $R^{1b}$ is —H, alkyl or substituted alkyl; $Z''$ is a halogen and —X—R—Y is para to —$B(OH)_2$.

7. The method of claim 6 wherein X is —$CZ''_2$—, —$CHZ''$—, —COO—, —$CONR^{1b}$—, —CO—, or —$SO_2$—.

8. The method of claim 6 wherein X is —CO—, R is a substituted or unsubstituted straight chained hydrocarbyl group comprising one or more amine or ammonium linking groups, and Y is —H, an amine or an ammonium group.

9. The method of claim 8 wherein R is an unsubstituted straight chained hydrocarbyl group comprising one ammonium linking group; Y is —H; and Phenyl Ring A is substituted with one or more groups $R_2$, wherein each $R_2$ is an electron withdrawing group and is independently selected.

10. A method claim 1, wherein the compound is represented by the following structural formula:

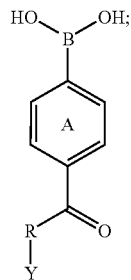

or a pharmaceutically acceptable salt thereof, wherein:

Phenyl Ring A is substituted or unsubstituted; and

R is a substituted or unsubstituted straight chained hydrocarbyl group optionally comprising one or more ether, thioether, phenylene, amine, or ammonium linking groups; and Y is an amine or ammonium group covalently bonded to the terminal position of R.

11. The method of claim 10 wherein R is —$CH_2$—O[—$(CH_2)_pO]_m$—$(CH_2)_p$— or —$CH_2$—S[—$(CH_2)_pO]_m$—$(CH_2)_p$—; p is 2 or 3; and m is an integer from 1–8.

12. The method of claim 11 wherein R is a straight chained hydrocarbyl group optionally comprising one or more ether or thioether linking groups.

13. The method of claim 12 wherein Phenyl Ring A is optionally substituted with one or more groups $R_2$, wherein each $R_2$ is an electron withdrawing group and is independently selected.

14. The method of claim 13 wherein R is an unsubstituted straight chained hydrocarbyl group optionally comprising one ether or one thioether linking group and Y is a trialkylammonium group.

15. The method of claim 10 wherein Phenyl Ring A is substituted with one or two groups $R_2$ and each $R_2$ is —F.

16. The method of claim 1, wherein the compound is represented by the following structural formula:

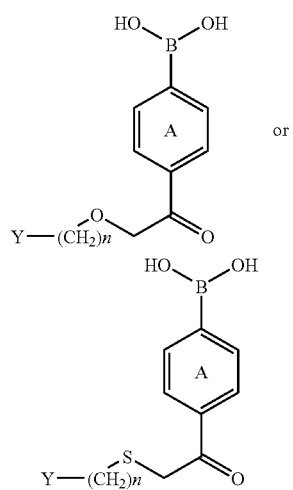

or a pharmaceutically acceptable salt thereof, wherein Y is a trialkylammonium group; n is an integer from about 6 to about 30; and Phenyl Ring A is substituted with one or two groups $R_2$, wherein each $R_2$ is an electron withdrawing group and is independently selected.

17. The method of claim 16 wherein Y is a trimethylammonium group and Phenyl Ring A is substituted with up to two fluorine groups.

18. The method of claim 17 wherein the compound is represented by the following structural formula:

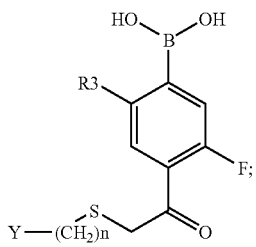

wherein $R_3$ is —H or —F.

19. A method of inhibiting the uptake of fat in the gastrointestinal tract of a subject afflicted with a condition selected from the group consisting of Type II diabetes mellitus, impaired glucose tolerance, hypertension, coronary thrombosis, stroke, lipid syndromes, hyperglycemia, hypertriglyceridemia, hyperlipidemia, sleep apnea, hiatal hernia, reflux esophagisitis, osteoarthritis, gout, cancers associated with weight gain, gallstones, kidney stones, pulmonary hypertension, infertility and cardiovascular disease, the method comprising the step of administering to the subject an effective amount of a compound represented by the following structural formula:

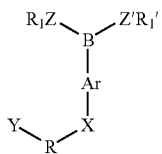

or a pharmaceutically acceptable salt thereof, wherein:

Z and Z' are independently —O—, —NH— or —S—;

Ar is a substituted or unsubstituted aryl group;

X is an electron withdrawing group;

R is a substituted or unsubstituted straight chained hydrocarbyl group optionally comprising one or more amine, ammonium, ether, thioether or phenylene linking groups;

Y is —H, an amine, —[NH—$(CH_2)_q]_r$—$NH_2$, halogen, —$CF_3$, thiol, ammonium, —OH, —COOH, —$SO_3H$, —$OSO_3H$ or phosphonium group covalently bonded to the terminal position of R, provided that when Y is —H and R is a straight chained hydrocarbyl group, then R has from 1 to 30 carbon atoms, and provided that each —NH— in —[NH—$(CH_2)_q]_r$—$NH_2$ is optionally N-alkylated or N,N-dialkylated and —$NH_2$ in —[NH—$(CH_2)_q]_r$—$NH_2$ is optionally N-alkylated, N,N-dialkylated or N,N,N-trialkylated;

q is an integer from 2 to about 10;

r is an integer from 1 to about 5;

$R_1$ and $R_1'$ are independently —H, an aliphatic group, a substituted aliphatic group, an aryl group or a substituted aryl group or, taken together, are a C2–C5 substituted or unsubstituted alkylene group optionally comprising an amine linking group [—$N^+(R^{1a})$—]; and $R^{1a}$ is —H, alkyl, substituted alkyl, phenyl or substituted phenyl.

20. The method of claim 1, wherein the condition is Type II diabetes mellitus.

21. The method of claim 1, wherein the condition is impaired glucose tolerence.

22. The method of claim 1, wherein the condition is hypertension.

23. The method of claim 1, wherein the condition is coronary thrombosis.

24. The method of claim 1, wherein the condition is stroke.

25. The method of claim 1, wherein the condition is a lipid syndrome.

26. The method of claim 1, wherein the condition is hyperglycemia.

27. The method of claim 1, wherein the condition is hypertriglyceridemia.

28. The method of claim 1, wherein the condition is hyperlipidemia.

29. The method of claim 1, wherein the condition is sleep apnea.

30. The method of claim 1, wherein the condition is hiatal hernia.

31. The method of claim 1, wherein the condition is reflux esophagisitis.

32. The method of claim 1, wherein the condition is osteoarthritis.

33. The method of claim 1, wherein the condition is gout.

34. The method of claim 1, wherein the condition is gallstones.

35. The method of claim 1, wherein the condition is kidney stones.

36. The method of claim 1, wherein the condition is pulmonery hypertension.

37. The method of claim 1, wherein the condition is infertility.

38. The method of claim 1, wherein the condition is a cardiovascular disease.

39. The method of claim 1, wherein the subject is obese.

* * * * *